US006143276A

United States Patent [19]

Unger

[11] Patent Number: 6,143,276
[45] Date of Patent: Nov. 7, 2000

[54] METHODS FOR DELIVERING BIOACTIVE AGENTS TO REGIONS OF ELEVATED TEMPERATURES

[75] Inventor: Evan C. Unger, Tucson, Ariz.

[73] Assignee: ImaRx Pharmaceutical Corp., Tucson, Ariz.

[21] Appl. No.: 08/823,791

[22] Filed: Mar. 21, 1997

[51] Int. Cl.[7] .................. A61B 5/055; A61K 49/04; A61K 9/127; A61K 9/14
[52] U.S. Cl. .................. 424/9.3; 424/9.4; 424/9.52; 424/450; 424/455; 424/491; 424/489; 424/497; 424/499; 424/502
[58] Field of Search .................. 424/9.52, 9.51, 424/450, 489, 502, 9.5, 455, 491, 497, 499, 9.3, 9.32, 9.321, 9.4; 514/743, 2, 957, 895, 904, 924, 929, 930

[56] References Cited

U.S. PATENT DOCUMENTS

| | | | |
|---|---|---|---|
| 3,015,128 | 1/1962 | Sommerville et al. | 18/2.6 |
| 3,291,843 | 12/1966 | Fritz et al. | 260/614 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,557,294 | 1/1971 | Dear et al. | 424/342 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,427,649 | 1/1984 | Dingle et al. | 424/38 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,530,360 | 7/1985 | Duarte | 128/419 F |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/1 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,663,161 | 5/1987 | Mannino et al. | 424/89 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,693,999 | 9/1987 | Axelsson et al. | 514/174 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,834,964 | 5/1989 | Rosen | 424/9 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 052 575 | 5/1982 | European Pat. Off. . |

(List continued on next page.)

OTHER PUBLICATIONS

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

(List continued on next page.)

*Primary Examiner*—Jose' G. Dees
*Assistant Examiner*—Michael G. Hartley
*Attorney, Agent, or Firm*—Woodcock, Washburn, Kurtz, Mackiewicz & Norris LLP

[57] ABSTRACT

Novel methods for delivering bioactive agents to particular regions or tissues of the body of a patient are provided.

60 Claims, 4 Drawing Sheets

U.S. PATENT DOCUMENTS

| | | | |
|---|---|---|---|
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,918,065 | 4/1990 | Stindl et al. | 514/179 |
| 4,919,895 | 4/1990 | Heldebrandt et al. | 422/129 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/9 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,372 | 9/1996 | Talish et al. | 601/2 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,571,797 | 11/1996 | Ohno et al. | 514/44 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,593,680 | 1/1997 | Bara et al. | 424/401 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,612,057 | 3/1997 | Lanza et al. | 424/450 |
| 5,612,318 | 3/1997 | Weichselbaum et al. | 514/44 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |
| 5,686,102 | 11/1997 | Gross et al. | 424/450 |
| 5,707,606 | 1/1998 | Quay | 424/9.52 |
| 5,707,607 | 1/1998 | Quay | 424/9.52 |
| 5,711,933 | 1/1998 | Bichon et al. | 424/9.52 |
| 5,716,597 | 2/1998 | Lohrmann et al. | 424/9.5 |
| 5,732,707 | 3/1998 | Widder et al. | 128/661.08 |
| 5,733,527 | 3/1998 | Schutt | 424/9.52 |
| 5,740,807 | 4/1998 | Porter | 128/662.02 |
| 5,804,162 | 9/1998 | Kabalnov et al. | 424/9.51 |
| 5,840,023 | 11/1998 | Oraevsky et al. | 600/407 |
| 5,858,399 | 1/1999 | Lanza et al. | 424/450 |

| | | |
|---|---|---|
| 5,885,865 | 1/1999 | Lambert et al. ............... 424/9.52 |
| B1 4,229,360 | 11/1991 | Schneider et al. ............... 260/403 |

FOREIGN PATENT DOCUMENTS

| | | |
|---|---|---|
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 727 225 A2 | 8/1996 | European Pat. Off. . |
| 2 700 952 | 8/1994 | France . |
| 25 21 003 | 8/1976 | Germany . |
| 62-286534 | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/09829 | 5/1994 | WIPO . |
| WO 84/02909 | 8/1994 | WIPO . |
| WO 94/16739 | 8/1994 | WIPO . |
| WO 94/21302 | 9/1994 | WIPO . |
| WO 94/28780 | 12/1994 | WIPO . |
| WO 94/28873 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/36286 | 11/1996 | WIPO . |
| WO 96/40281 | 12/1996 | WIPO . |
| WO 98/00172 | 1/1998 | WIPO . |

OTHER PUBLICATIONS

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Facture Model", *J. Orthopaedic Res.*, 1996, 14(5), 802–809.

Young et al., "Effect of therpeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Hynynen et al., "The Usefulness of a Contrast Agent and Gradient Recalled Acquisition in a Steady–State Imaging Sequence for Magnetic Resonance Imaging–Guided Non-invasive Ultrasound Surgery", *Investigative Radiology*, 1994, 29(10), 897–903.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Desir et al., "Assessment of regional myocardial perfusion with myocardial contrast echocardiography in a canine model of varying degrees of coronary stenosis", *Am. Heart J.*, Jan., 1994, 127(1), 56–63.

Sekins et al., "Lung Cancer Hyperthermia via Ultrasound and PFC Liquids", Published in Proceedings of 5th International Symposium on Hyperthermic Oncology, Kyoto, Japan, Aug. 29–Sep. 3, 1998, 3 pages.

Pietersen, "A New Warning System for Fires of Electrical Origin", *CERN European Organization for Nuclear Research, Health and Safety Division*, Mar., 1977, 1–5.

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, 65(2):458–465 (1989).

Lincoff et al., "Perfluoro–n–butane: A Gas for Maximun Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Consise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Bio–chemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochemica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigation Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 30–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiably Low–frequency Synthesized Ultrasound", *IEEE Engineering*, pp. 879–880, vol. 2 (1988) (abstract).

McAvoy et al., IEEE Engineering, Ultrasonics Symposium Proceedings, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.

Mathiowitz et al., "Photochemical Rupture of Microcapsules: A Model System", *Journal of Applied Polmyer Science*, 1981, 26:810–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS 13463*, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian *Tomography*, Kee, et al., n, "Physical Principles and Instrumentation", *Computed Body* eds., Raven Press, New York, Chapter 1, pp. 1–7 (1988).

Aronberg, "Techniques", *Computed Body Tomography*, Kee, et al., eds, Raven Press, New York, Chapter 2, pp. 9–36 (1988).

Miller, *Ultrasonics* (Sep. 1981), "Ultrasonic detection of resonant cavitation bubbles in a flow tube by their second––harmonic emissions," pp. 217–224.

Dittrich, "Cardiac Muscle Ischemia and Infarction", The Second Annual International Symposium on Contrast Agents in Diagnostic Ultrasound, Atlantic City, NJ (May 7, 1996) (abstract).

Pantely, "Intravenous Contrast Echocardiography–Tissue Imaging & Quantification of Coronary Blood Flow", The Second Annual International Symposium on Contrast Agents in Diagnostic Ultrasound, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorniated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang et al., "Semipermeable Aqueous Microcapsules", *Canadian J. Of Phys. And Pharm.*, 1996, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al, "Preparation of Microencapsulated Liposomes", *J. Microencapsulation*, 1988, 5, 331–337.

Mattrey et al., *Gas Emulsions as Ultrasound Contrast Agents: Preliminary Results in Rabbits and Dogs, Investigative Radiology*, vol. 29, Jun. Supp. 2, pp. S139–S141, 1994.

Meltzer et al., *Transmission of Ultrasonic Contrast Through the Lungs, Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

METHODS FOR DELIVERING BIOACTIVE AGENTS TO REGIONS OF ELEVATED TEMPERATURES

BACKGROUND OF THE INVENTION

1. Field of the Invention

The present invention relates to methods for delivering bioactive agents, in particular to methods for delivering bioactive agents to specific regions of the body of a patient.

2. Background of the Invention

Treatment modalities for certain diseases often rely on the ability to target bioactive agents to a diseased region or tissue in the body of a patient, while minimizing or preventing action of the bioactive agents on other regions or tissues in the body, such as undiseased regions or tissues. Examples of bioactive agents which may be targeted to specific regions of the body of a patient include pharmaceutical and diagnostic agents.

Current methods for targeted delivery of bioactive agents are reviewed, for example, in Cronstein and Weissman, "Targets for Anti-inflammatory Drugs", *Ann. Rev. Pharmacol. Toxicol.* 35:449–62 (1995). One method involves the use of liposomes as delivery vehicles, in which the lipid moiety of the liposome undergoes a phase transition at about 42° C. External heat is applied to produce the necessary temperature increase to induce the phase transition. Specific applications of the use of liposomes for targeted delivery of bioactive agents include treatment of disorders of the eye (see, e.g., Khoobehi, et al., *Jpn. J. Ophthamol.* 33:405–412 (1989)), and treatment of tumors (see, e.g., Maekawa et al., *Cancer Treatment Reports* 71:1053–59 (1987)). However, as discussed in Magin et al., *Cancer Drug Delivery* 3:223–37 (1986), the use of liposomes for targeted drug delivery is limited by the inability of the liposomes to clear the reticuloendothelial system. A further limitation of the method is the necessity of applying external heat to obtain a temperature of 42° C. or higher.

Structural features, such as tumor antigens, are also used in targeting delivery of a bioactive agent to a particular region or tissue. However, such structural features are associated with one or, at most a few, disease states. In addition, incomplete or irregular expression of such structural features may further limit their usefulness in targeted delivery of bioactive agents.

Accordingly, a need continues for new and/or improved methods for targeting specific regions or tissues in the body of a patient, and delivering bioactive agents to the targeted regions or tissues. The present invention is directed to these, as well as other, important ends.

SUMMARY OF THE INVENTION

The present invention is directed, in part, to new and/or improved methods for delivering bioactive agents, in particular to methods for delivering bioactive agents to specific regions of a patient's body. The present invention is highly unique in that, among other things, it takes advantage of the presence of elevated bodily temperatures at a site of, for example, disease, infection or injury to allow specific targeting and delivery of a bioactive agent to those sites.

Specifically, in one embodiment, there is provided a method for delivering a bioactive agent to a region of a patient comprising administering to the patient a composition comprising a bioactive agent and a gaseous precursor capable of undergoing phase transition to a gas at a region of elevated temperature in the patient. If desired, the composition may further comprise a stabilizing material. The stabilizing material may, if desired, be in the form of a vesicle, and may also, if desired, be non-vesicular.

In another embodiment of the invention, there is provided a method for imaging a region of a patient comprising administering to the patient a composition comprising a gaseous precursor capable of undergoing phase transition to a gas at a region of elevated temperature in the patient, and scanning the patient using diagnostic imaging. If desired, the composition may further comprise a stabilizing material, with the stabilizing material being vesicular or non-vesicular, as desired. Also, a bioactive agent, such as a diagnostic agent may be further included.

In a further embodiment, the invention pertains to a method for diagnosing the presence of diseased tissue in a region of a patient comprising administering to the patient a composition comprising a diagnostic agent and a gaseous precursor capable of undergoing phase transition to a gas at a region of elevated temperature in the patient, and scanning the patient using diagnostic imaging. If desired, the composition may further comprise a stabilizing material, with the stabilizing material being in the form of a vesicle or non-vesicular as desired. Also, a bioactive agent, such as a diagnostic agent, may be further included.

Still further, the present invention is directed to a method for treating a patient comprising administering to the patient a composition comprising a pharmaceutical agent and a gaseous precursor capable of undergoing a phase transition to a gas at a region of elevated temperature in the patient.

These and other aspects of the invention will be made apparent by the application as a whole.

BRIEF DESCRIPTION OF THE DRAWINGS

As shown in FIG. 1 there is a substantial increase in particle diameter as it enters the region of increased temperature. Drug dissociation from the particle occurs within the region of tissue with elevated temperature.

DETAILED DESCRIPTION OF THE INVENTION

Figure 1:
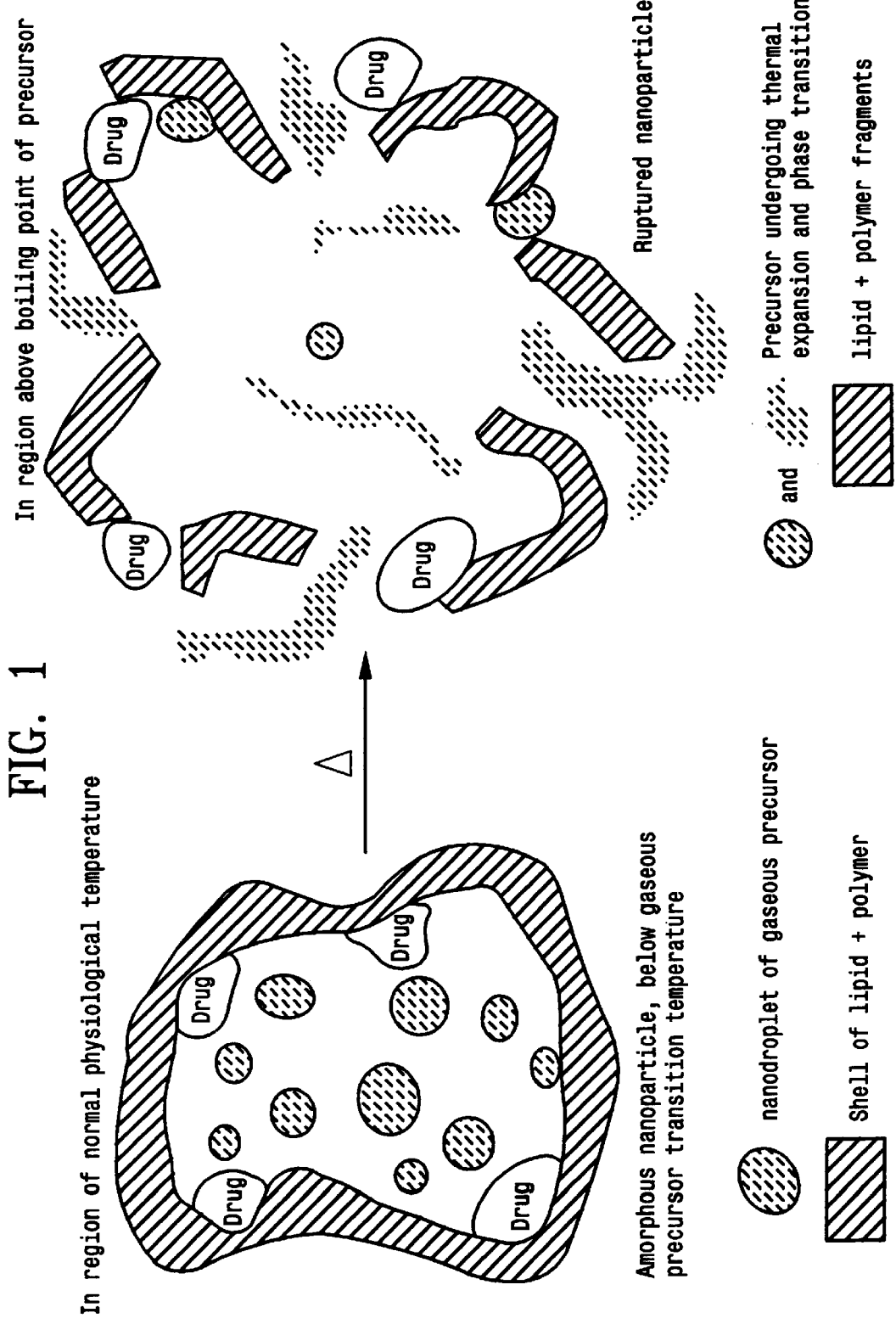
FIG. 1 is a diagram of a nanoparticle with a central core of gaseous precursor and a wall of stabilizing material and imbedded drug.
Figure 2:
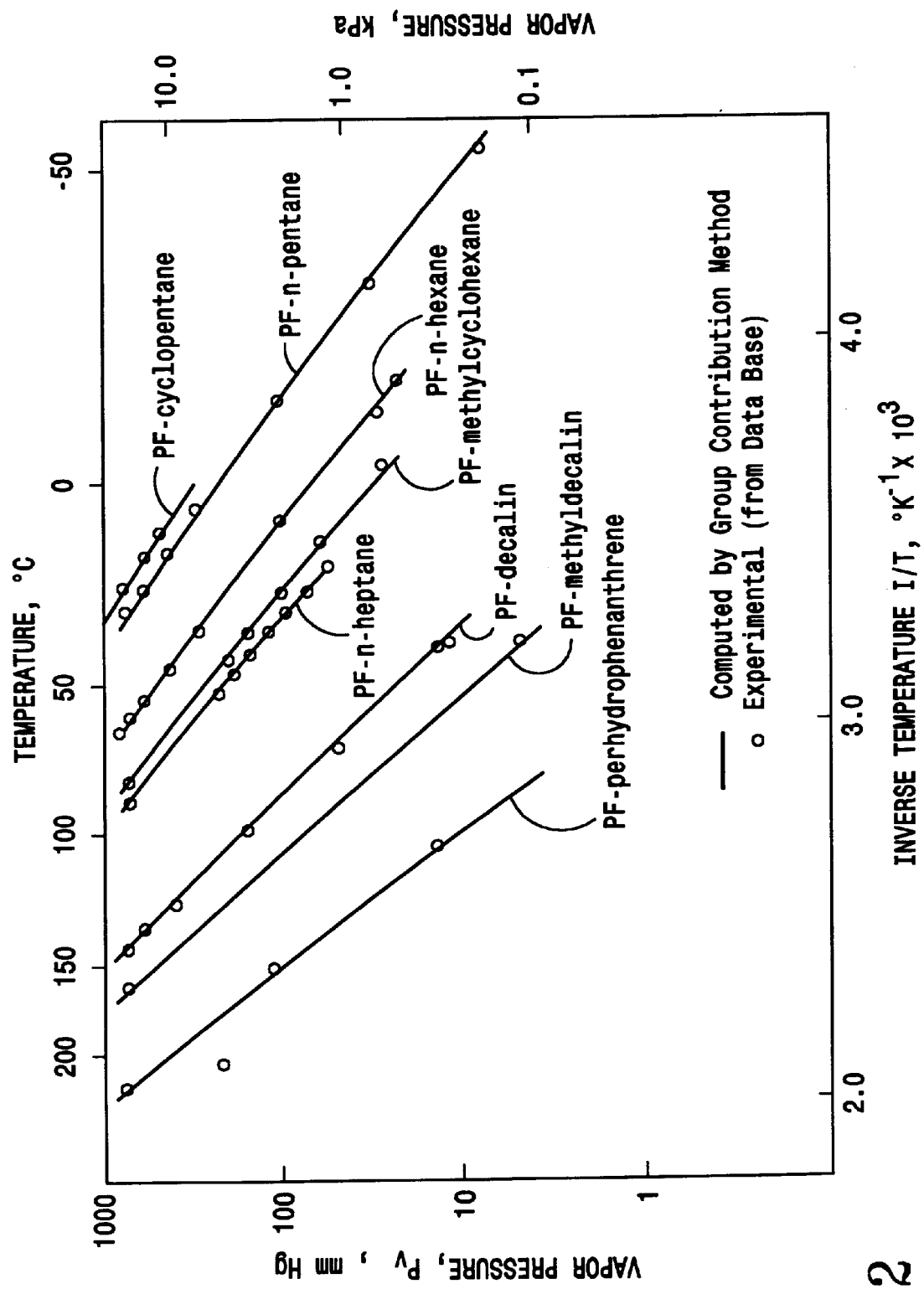
FIG. 2 is a graphical representation of the relationship between vapor pressure and temperature. Data from Kelly, et al., *Ind. Eng. Chem. Res.* (1988) 27:1732–1735.

As employed herein and throughout the disclosure, the following terms, unless otherwise indicated, shall be understood to have the following meanings. "Lipid" refers to a naturally-occurring, synthetic, or semi-synthetic (i.e., modified natural), compound which is generally amphipathic. The lipids typically comprise a hydrophilic component and a hydrophobic component. Exemplary lipids include, for example, fatty acids, neutral fats, phosphatides, oils, glycolipids, fluorolipids, surface-active agents (surfactants), aliphatic alcohols, waxes, terpenes and steroids. The phrase semi-synthetic (or modified natural), as employed herein, denotes a natural compound that has been chemically modified in some fashion. "Protein", as used herein, refers to molecules comprising, and preferably consisting essentially of, α-amino acids in peptide linkages. Included within the term "protein" are globular proteins such as albumins, globulins and histones, and fibrous proteins such as collagens, elastins and keratins. Also included are "compound proteins", wherein a protein molecule is united with a nonprotein molecule, such as nucleoproteins, mucoproteins, lipoproteins and metalloproteins. The proteins may be naturally-occurring, synthetic, or semi-synthetic.

"Polymer" or "polymeric", as used herein, refers to molecules formed from the chemical union of two or more repeating units. Accordingly, included within the term "polymer" may be, for example, dimers, trimers and oligomers. The polymer may be naturally-occurring, synthetic, or semisynthetic. In preferred form, the term "polymer" refers to molecules which comprise 10 or more repeating units.

"Stabilizing material" or "stabilizing compound", as used herein, refers to any material which is capable of improving the stability of compositions containing the gaseous precursor and bioactive agent as described herein, including, for example, mixtures, suspensions, emulsions, dispersions, vesicle compositions, or the like. The improved stability involves, for example, the maintenance of a relatively balanced condition, and may be exemplified, for example, by increased resistance of the composition against destruction, decomposition, degradation, and the like. In the case of preferred embodiments involving vesicles filled with gaseous precursor and/or bioactive agent, the stabilizing compounds may serve to either form the vesicles or stabilize the vesicles, in either way serving to minimize or substantially (including completely) prevent the escape of gaseous precursor and/or bioactive agent from the vesicles until said release is desired. The term "substantially", as used in the present context of preventing escape of gaseous precursor and/or bioactive agent from said vesicles, means greater than about 50%, is maintained entrapped in the vesicles until release is desired, and preferably greater than 60%, more preferably greater than about 70%, even more preferably greater than about 80%, still even more preferably greater than about 90%, is maintained entrapped in the vesicles until release is desired. In particularly preferred embodiments, greater than about 95% of the gaseous precursor and/or bioactive agent is maintained entrapped until release is desired. The gaseous precursor and/or bioactive agent may also be completely maintained entrapped (i.e., about 100% is maintained entrapped), until release is desired.

Exemplary stabilizing materials include, for example, lipids, proteins, polymers, carbohydrates, and surfactants. The resulting mixture, suspension, or emulsion or the like may comprise walls (i.e., films, membranes and the like) around the bioactive agent and/or gaseous precursor, or be substantially devoid of walls or membranes, if desired. The stabilizing material may, if desired, form droplets. The stabilizing material may also comprise salts and/or sugars. In certain embodiments, the stabilizing materials may be substantially (including completely) cross-linked.

The terms "cross-link", "cross-linked" and "cross-linking", as used herein, generally refer to the linking of two or more stabilizing materials, including lipid, protein, polymer, carbohydrate and surfactant stabilizing materials, by one or more bridges. The bridges, which may be composed of one or more elements, groups, or compounds, generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in materials formulated from peptide chains which are joined by disulfide bonds of cystine residues, as in keratins, insulin, and other proteins. Alternatively, cross-linking may be effected by suitable chemical modification, such as, for example, by combining a compound, such as a stabilizing material, and a chemical substance that may serve as a cross-linking agent, which may be cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds may be substantially cross-linked. The term "substantially", as used in reference to cross-linked stabilizing compounds, means greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., greater than about 50% of the stabilizing compounds, are devoid of cross-linking bridges, and if desired, greater than about 60%, 70%, 80%, 90%, 95%, or even 100% of the stabilizing compounds are devoid of cross-linking bridges.

"Vesicle" refers to an entity which is generally characterized by the presence of one or more walls or membranes which form one or more internal voids. Vesicles may be formulated, for example, from a stabilizing material such as a lipid, including the various lipids described herein, a proteinaceous material, including the various proteins described herein, a polymeric material, including the various polymeric materials described herein. As discussed herein, vesicles may also be formulated from carbohydrates, surfactants, and other stabilizing materials, as desired. The lipids, proteins, polymers and/or other vesicle forming stabilizing materials may be natural, synthetic or semi-synthetic. Preferred vesicles are those which comprise walls or membranes formulated from lipids. The walls or membranes may be concentric or otherwise. The stabilizing compounds may be in the form of a monolayer or bilayer, and the monolayer or bilayer lipids may be used to form one or more monolayers or bilayers. In the case of more than one monolayer or bilayer, the monolayers or bilayers may be concentric if desired. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The vesicles described herein include such entities commonly referred to as, for example, liposomes, micelles, bubbles, microbubbles, microspheres, lipid-, polymer- and/or protein-coated bubbles, microbubbles and/or microspheres, nanospheres, microballoons, microcapsules, aerogels, clathrate bound vesicles, hexagonal H II phase structures, and the like. The internal void of the vesicles may be filled with a gaseous precursor and a bioactive agent, if desired, and/or other materials. The vesicles may also comprise a targeting ligand, if desired.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes which are formulated from non-ionic lipids may also be referred to as "niosomes."

"Micelle" refers to colloidal entities formulated from lipids. In certain preferred embodiments, the micelles comprise a monolayer or hexagonal H II phase configuration. In other preferred embodiments, the micelles may comprise a bilayer configuration.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In preferred form, the clathrates may form a cage-like structure containing cavities which comprise the vesicles. One or more vesicles may be bound to the clathrate, if desired. A stabilizing material may, if desired, be associated with the clathrate to promote the association of the vesicle with the clathrate. Suitable materials from which clathrates may be formulated include, for example, porous apatites, such as calcium hydroxyapatite, and precipitates of polymers and metal ions, such as alginic acid precipitated with calcium salts.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including mono- or bilayers.

"Suspension" or "dispersion" refers to a mixture, preferably finely divided, of two or more phases, (solid, liquid or gas), such as, for example, liquid in liquid, solid in solid, gas in liquid, and the like, which preferably can remain stable for extended periods of time.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube. The hydrophobic portion (s) of the lipids generally radiate outwardly and the complex assumes the shape of a hexagonal tube. A plurality of tubes is generally packed together in the hexagonal phase structure.

As discussed in detail below, the compositions and formulations of this invention may be administered to a patient. As used herein, "patient" refers to animals, including mammals, preferably humans.

The phrase "region of a patient", as used herein refers to a particular area or portion of the patient and in some instances to regions throughout the entire patient. Exemplary of such regions are the gastrointestinal region, the cardiovascular region (including myocardial tissue), the renal region as well as other bodily regions, tissues, organs and the like, including the vasculature and circulatory system, and as well as diseased tissue, including cancerous tissue. Regions of a patient include, for example, regions to be targeted for delivery of a bioactive agent, regions to be imaged using diagnostic imaging, and regions of elevated temperature. The region of the patient is preferably internal, although, if desired, it may be external. The phrase "cardiovascular region" refers to the region of the patient defined by the heart (myocardium) and the vasculature leading directly to and from the heart. The phrase "vasculature" denotes blood vessels (including arteries, veins, and the like). The phrase "gastrointestinal region" includes the region defined by the esophagus, stomach, small and large intestines, and rectum. The phrase "renal region", as used herein, denotes the region defined by the kidney and the vasculature that leads directly to and from the kidney, and includes the abdominal aorta.

"Region of elevated temperature" as used herein in connection with a patient, refers to a region exhibiting a condition of elevated temperature above that of the normal bodily temperature of the region. Elevated temperature conditions can result, for example, from disease, infection, injury, etc., and include fever and inflammation states. By way of example, bacterial, viral, fungal, parasitic or other microorganismal invasion may result in an increased temperature, particularly at the site of infection. Arthritis, cancer and the presence of cardiovascular plaques may also result in increased temperature conditions. Exposure to heat, radiation, fire, etc. resulting, for example, in a burn condition, may also cause elevated temperature regions. Localized physical injuries such as tissue trauma, tears, breaks, etc., may also result in regionalized conditions of increased temperature. "Region to be targeted" or "targeted region" refer to a region of a patient where delivery of a bioactive agent is desired. "Region to be imaged" or "imaging region" denotes a region of a patient where diagnostic imaging is desired.

"Bioactive agent" refers to a substance which may be used in connection with an application that is therapeutic or diagnostic in nature, such as, for example, in methods for diagnosing the presence or absence of a disease in a patient or in methods for the treatment of disease in a patient. As used herein, "bioactive agent" refers also to substances which are capable of exerting a biological effect in vitro and/or in vivo. The bioactive agents may be neutral, or positively or negatively charged. Examples of suitable bioactive agents include diagnostic and pharmaceutical agents, including drugs, synthetic organic molecules, proteins, peptides, vitamins, steroids, steroid analogs; and genetic material, including nucleosides, nucleotides and polynucleotides.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound imaging, magnetic resonance imaging or computed tomography imaging of a patient. Diagnostic agents may also include any other agents useful in facilitating diagnosis of a disease or other condition in a patient, whether or not imaging methodology is employed.

"Pharmaceutical agent" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term pharmaceutical or drug.

"Targeting ligand" refers to any material or substance which may promote targeting of tissues and/or receptors in vitro or in vivo with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, such as saccharides, including mono- and polysaccharides, and carbohydrates, vitamins, steroids, steroid analogs, hormones, cofactors, bioactive agents, and genetic material, including nucleosides, nucleotides, nucleotide acid constructs, and polynucleotides.

"Thickening agent" refers to any of a variety of generally hydrophilic materials which, when incorporated in the lipid, polymer, protein and/or vesicle compositions and/or formulations described herein, may act as viscosity modifying agents, emulsifying and/or solubilizing agents, suspending agents, and tonicity raising agents. It is contemplated that the thickening agents may be capable of aiding in maintaining the stability of the compositions due to such properties.

"Dispersing agent" refers to a surface-active agent which, when added to a suspending medium of colloidal particles, including, for example, certain of the lipid, polymer, protein, and/or vesicle compositions described herein, may promote uniform separation of particles. In certain preferred embodiments, the dispersing agent may comprise a polymeric siloxane compound, such as, for example, polydimethylsiloxane (i.e., simethicone).

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant or other technology, or by a combination thereof. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA, as well as catalytic RNA.

The terms "administered" and "administration" refer generally to the administration to a patient of a biocompatible material, including, for example, the lipid, polymer, protein, and/or vesicle compositions described herein.

"Biocompatible" refers to materials which are generally not injurious to biological functions and which will not result in any degree of unacceptable toxicity, including allergenic responses and disease states. The compositions and components thereof (such as stabilizing materials, gaseous precursors, and bioactive agents, etc.) employed in the present invention are typically biocompatible.

"Droplet", as used herein, refers to a spherical or spheroidal entity which may be substantially liquid or which may comprise liquid and solid, liquid and gas, or liquid, solid and gas. Solid materials within a droplet may be, for example, particles, polymers, lipids, or proteins.

"Nano" or "nanoparticle", as used herein, refers to particles and the like having a diameter of less than about one micrometer. "Micro" or "microparticle", as used herein, refers to particles and the like having a diameter of about one micrometer or greater, typically up to about 10 micrometers. The terms "nanodroplet" and "microdroplet", as used herein, refer to droplets having a diameter of less than about 1 micrometer or of 1 micrometer or greater, respectively. Similarly, the terms "nanosphere" and "microsphere" may be used to refer to approximately spherical structures having a diameter of less than about 1 micrometer or of 1 micrometer or greater, respectively.

"In combination with" refers to the co-administration of a bioactive agent with the gaseous precursor (and stabilizing material, if desired). The bioactive agent may be combined with the gaseous precursor (and stabilizing agent) in any of a variety of different ways. For example, in the case of stabilizing materials forming vesicles, the bioactive agent and/or gaseous precursor may be entrapped within an internal void of the vesicle. In addition, the bioactive agent may be integrated within the layer(s) or wall(s) of the vesicle, for example, by being interspersed among stabilizing materials which form the vesicle layer(s) or wall(s). It is also contemplated that the bioactive agent may be located on the surface of a vesicle or non-vesicular stabilizing material. In this case, the bioactive agent may interact chemically with the inner or outer surface of the vesicle and remain substantially adhered thereto. Such interaction may take the form of, for example, non-covalent association or bonding, ionic interactions, electrostatic interactions, dipole-dipole interactions, hydrogen bonding, van der Waal's forces, covalent association or bonding , cross-linking or any other interaction, as will be readily apparent to one skilled in the art, once armed with the present disclosure. Also, the bioactive agent may interact with the inner or outer surface of the vesicle or the non-vesicular stabilizing material in a limited manner. Such limited interaction would permit migration of the bioactive agent, for example, from the surface of a first vesicle to the surface of a second vesicle, or from the surface of a first non-vesicular stabilizing material to a second non-vesicular stabilizing material.

A "gaseous precursor", within the context of the present invention, is preferably a liquid at the temperature of manufacture or storage, but forms a gas at an elevated temperature under physiological conditions (such as in a region of elevated temperature of a patient). However, compounds which are a solid at the temperature of manufacture or storage, but which form a gas at an elevated temperature under physiological conditions, are also within the scope of this invention. Such liquid or solid materials may also be referred to herein as "temperature activated gaseous precursors". A liquid to gas phase transition temperature is also referred to herein as a boiling point.

The vesicles employed in the methods of the present invention preferably contain a gaseous precursor. "Gaseous precursor filled vesicle" refers to vesicles in which there is encapsulated a gaseous precursor. In certain preferred embodiments, the vesicles may be substantially (including completely) filled with the gaseous precursor. The term "substantially", as used in reference to the amount of gaseous precursor in the gaseous precursor filled vesicles, means that greater than about 30% of the internal void volume of the vesicle consists of a gaseous precursor. In certain embodiments, preferably, greater than about 40% of the internal void of the substantially filled vesicles consists of a gaseous precursor, with greater than about 50% being more preferred. Even more preferably, greater than about 60% of the internal void of the substantially filled vesicles consists of a gaseous precursor, with greater than about 70% being still more preferred. In certain particularly preferred embodiments, greater than about 75%, 85% or even 95% of the internal void of the vesicles consists of a gaseous precursor. If desired, the substantially filled vesicle may be completely filled (i.e. filled with about 100% gaseous precursor). Although not considered a preferred embodiment of the invention, the vesicles may also contain, if desired, no or substantially no gaseous precursor.

While not intending to be bound by any particular theory of operation, the methods of the present invention rely, in part, on the phenomenon of elevated local temperature typically associated with disease, inflammation, infection, etc. as discussed herein. Such conditions, which may also be referred to as physiological stress states, may elevate the temperature in a region of the patient, by a fraction of a degree or as much as 1, 2, 3, 4, 5, 6, 7, 8, 9, 10, or more degrees. For example, although normal human body temperature is about 37° C., tissue affected by disease, inflammation, infection, etc. can have temperatures greater than about 37° C., such as, for example, about 40° C. By incorporating materials which are liquid at normal physiological temperatures (i.e. the temperature of a particular mammal under normal circumstances) and which undergo a phase transition to form a gas at the elevated temperature, the methods of the present invention allow bioactive agents to be effectively delivered to the affected tissue and advantageously released at that site. When the gaseous precursor, for example, undergoes a phase transition from a liquid or solid to a gas, bioactive agents carried within the gaseous precursor may be released into the region of the tissue thereby effecting delivery of the bioactive agent to the region of need. Thus, in accordance with the present method, other regions of the patient not affected by the regionalized condition of increased temperature are bypassed, and the bioactive agent is selectively delivered to the region in need.

Indeed, the present invention is intended to take advantage of the sensitivity of the gaseous precursors to temperature and their ability to undergo a phase transition to form a gas at a defined temperature. As this phase transition occurs, bioactive agents are released from the composition of the invention to the desired region of the patient. Because the invention employs the fundamental physical property of elevated temperature, it has wide ranging applications to a variety of disease, infection, injury, fever, inflamed states, etc. which exhibit such elevated temperature conditions. While the present invention allows the use of targeting ligands to target specific regions of the body, such as antibodies or peptides, targeting ligands are generally not necessary since the gaseous precursor accomplishes delivery and targeting by virtue of local increase in temperature associated with the physiologically induced temperature change.

Bioactive agents for use in this invention may be soluble in the gaseous precursor. Compositions utilizing a soluble bioactive agent may be formed by, for example, dissolving the bioactive agent within the gaseous precursor at ambient temperature, and agitating and/or extruding the materials to prepare particles of the bioactive agent. The particles are preferably nanoparticles or microparticles. The formation of particles of bioactive agent and gaseous precursor works advantageously for hydrophobic bioactive agents.

Gaseous precursors for use in the present invention are preferably biocompatible, and preferably form biocompatible gases. Preferred gaseous precursors include organic compounds containing from 1 to about 8 carbon atoms, more preferably from about 2 to about 6 carbon atoms, although larger chain compounds may also be employed in appropriate circumstances. Suitable gaseous precursors may contain one or more heteroatoms such as oxygen atoms, halogen atoms, and the like.

Exemplary compounds containing mixed halogens, suitable for use in the present invention, include 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1,1,2,2,3,3,4,4-octafluorobutane, 1,1,1,3,3-pentafluorobutane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, 1-bromo-1,1,2,3,3,3-hexafluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, and heptafluoro-2-iodopropane. Fluorinated compounds useful in the present invention include 3-fluorobenzaldehyde, 2-fluoro-5-nitrotolune, 3-fluorostyrene, perfluoro-2-methyl-2-pentene, 3,5-difluoroaniline, 2,2,2-trifluoroethylacrylate, 30(trifluoromethoxy)-acetophenone, 1,1,2,2,3,3,4,4-octafluorobutane, 1,1,1,3,3-pentafluorobutane, perfluorocyclohexane, perfluoromethyl-n-butyl ether, perfluoromethylisopropyl ether, perfluoromethyl-t-butyl ether, 1-fluorobutane, 1-bromononafluorobutane, 4-trifluoromethyl perfluorotetrahydrofuran, perfluorotetrahydropyran, and perfluoropentane. Brominated compounds useful in the present invention include 1-bromoethane, 6-bromo-1-hexene, 2-bromo-2-nitropropane, 2-bromo-5-nitrothiophene, and 2-bromopropene. Chlorinated compounds useful in the present invention include 3-chloro-5,5-dimethyl-2-cyclohexene and 2-chloro-2-methylpropane. In addition, compounds having the structure $C_nF_yH_xOBr$, wherein n is an integer from 1 to 6, y is an integer from 0 to 13, and x is an integer from 0 to 13, are useful as gaseous precursors. Examples of useful gaseous precursors having this formula include perfluoropropyloxylbromide and 2-bromooxyperfluoropropane.

Also useful as gaseous precursors in the present invention are partially or fully fluorinated ethers, preferably having a boiling point of from about 36° C. to about 60° C. Fluorinated ethers are ethers in which one or more hydrogen atoms is replaced by a fluorine atom. For purposes of this invention, fluorinated ethers have the general formula $CX_3(CX_2)_n—(CX_2)_nCX_3$, wherein X is H, F or another halogen provided that at least one of X is fluorine. Generally, fluorinated ethers containing about 4 to about 6 carbon atoms will have a boiling point within the preferred range for the invention, although smaller or larger chain fluorinated ethers may also be employed in appropriate circumstances. Exemplary fluorinated ethers include compounds having the formulae $CF_3CF_2OCF_2CF_3$, $CF_3O(CF_2)_2CF_3$ and $CF_3OCF(CF)_2$.

Preferred gaseous precursors undergo phase transition to gas at a temperature of from greater than about 37° C. to about 52° C., preferably from about 38° C., to about 50° C., more preferably from about 38° C. to about 48° C., even more preferably from about 38° C. to about 46° C., still even more preferably from about 38° C. to about 44° C., even still more preferably from about 38° C. to about 42° C., and most preferably at a temperature of about 39° C., 40° C., or 41° C. As will be recognized by one skilled in the art, the optimal phase transition temperature of a gaseous precursor for use in a particular application will depend upon considerations such as, for example, the particular patient, the tissue being targeted, the nature of the physiological stress state (i.e., disease, infection or inflammation, etc.) causing the increased temperature, the stabilizing material used, and/or the nature of the bioactive agent to be delivered. Also, as one skilled in the art will recognize, the phase transition temperature of a compound may be affected by local conditions within the tissue, such as, for example, local pressure (for example, interstitial, interfacial, or other pressures in the region). By way of example, if the pressure within the tissues is higher than ambient pressure, this will be expected to raise the phase transition temperature. The extent of such effects may be estimated using standard gas law predictions, such as Charles' Law and Boyle's Law. As an approximation, compounds having a liquid-to-gas phase transition temperature between about 30° C. and about 50° C. can be expected to exhibit about a 1° C. increase in the phase transition temperature for every 25 mm Hg increase in pressure.

As a particular example, the liquid-to-gas phase transition temperature (boiling point) of 5 dodecafluoropentane (perfluoropentane) is measured at 29.5° C. at standard pressure (i.e. 760 mm Hg), but at interstitial pressure of 795 mm Hg, the boiling point is about 30.5° C.

Materials used in stabilizing the gaseous precursor, discussed more fully herein, may also affect the phase transition temperature of the gaseous precursor. In general, the stabilizing material is expected to increase the phase transition temperature of the gaseous precursor. In particular, a relatively rigid polymeric material, such as, for example, polycyanomethacrylate, may have a significant effect on the phase transition temperature of the gaseous precursor. Such an effect must be considered in the selection of the gaseous precursor and the stabilizing material.

In accordance with the present invention, the gaseous precursor is preferably stabilized by one or more biocompatible materials which, if desired, may be capable of forming a wall or membrane surrounding one or more internal voids (i.e., form a vesicle). For purposes of the present invention, the void preferably contains one or more gaseous precursors and, optionally, one or more bioactive agents. Exemplary compounds capable of forming a wall or membrane include lipids, proteins, polymers, carbohydrates, and surfactants. Such wall or membrane forming compounds may also include galactose and fluorinated sugars. Alternatively, stabilizing materials generally not capable of forming walls but which act by, for example, raising the viscosity or osmotic pressure of the surrounding medium, may be used. Examples of non-wall-forming stabilizing materials include salts and sugars. These non-wall forming materials may be used alone or in combination with other stabilizing materials which may be of the type which is capable of forming a wall or membrane. As will be recognized by those skilled in the art, the foregoing listed wall forming materials may, in appropriate circumstances, be employed as non-wall forming stabilizing agents, and vice versa.

Thus, stabilizing compounds which may be employed in the methods and compositions of the present invention include, for example, lipids (including fluorinated lipids), proteins, polymers, carbohydrates, and sugars (including fluorinated sugars), and such stabilizing compounds are preferred. Of course, as would be apparent to one of ordinary skill in the art, once armed with the teachings of the present disclosure, other stabilizing compounds, in addition to the aforementioned classes of compounds, can of course also be utilized. Broadly speaking, any of a wide variety of organic and inorganic materials may be employed as stabilizing materials in the methods and compositions of the present invention including, for example, solid materials, such as particulate materials including, for example, apatites, or liquid materials, such as oils, surfactants, and the like. The stabilizing compounds employed preferably include surfactants, tensides, suspending agents, emulsifying agents, tonicity modifying agents, viscosity modifying agents, antifoaming agents, thickeners, dispersing agents, solvents, diluents, and the like.

While it is not intended that the present invention be bound by any theory or theories, it is believed that the use of a stabilizing material, particularly a wall-forming stabilizing material, facilitates and enhances the association between the gaseous precursor and any bioactive agent to be used. However, if desired, a bioactive agent may be associated with one or more gaseous precursors without the requirement of a stabilizing agent. Where a bioactive agent and gaseous precursor are used alone (i.e., without a stabilizing agent), the composition may be prepared by, for example, admixing by mechanical means. Preferably, the mechanical means causes the gaseous precursor and the bioactive agent to form "microdroplets" or "nanodroplets". Examples of mechanical means by which the bioactive agent and gaseous precursor may be admixed include agitation by methods including stirring, sonication, vortexing, shaking, microemulsification, and extrusion. Mechanical means of agitation are discussed more fully herein. Of course, such means may also be employed to form compositions which also include stabilizing materials.

Compositions comprising lipids are particularly preferred as stabilizing materials for the gaseous precursors and bioactive agents. The lipid compositions may be, and are desirably, in the form of vesicles.

The gaseous precursors are preferably incorporated into the vesicular or nonvesicular stabilizing material compositions irrespective of the physical nature of the composition. Thus, it is contemplated that the gaseous precursors may be incorporated, for example, in lipid compositions in which the lipids are aggregated randomly, as well as in vesicle compositions, including vesicle compositions which are formulated from lipids, such as micelles and liposomes. Incorporation of the gaseous precursors in the lipid and/or vesicle compositions may be achieved by using any of a number of methods. For example, in the case of vesicles based on lipids, the formation of vesicles containing gaseous precursors can be achieved by shaking, emulsifying, or otherwise agitating an aqueous mixture which comprises a gaseous precursor and one or more lipids. This promotes the formation of stabilized vesicles within which the gaseous precursor is encapsulated.

It may be possible to enhance the stability of vesicles formulated from lipids by incorporating in the lipid compositions at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids may provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which may be proximate thereto. In this way, the vesicles may be less prone to come into touching proximity with each other, which may lead to a rupture of the membrane or skin of the vesicles and consolidation of the contacting vesicles into a single, larger vesicle. A continuation of this process of consolidation will, of course, lead to significant degradation of the vesicles.

A wide variety of lipids are believed to be suitable for incorporation in the lipid or vesicle compositions. With particular reference to vesicle compositions, for example, micelles and/or liposomes, any of the materials or combinations thereof which are known to those skilled in the art as suitable for their preparation may be used. The lipids used may be of natural, synthetic or semi-synthetic origin. As noted above, suitable lipids generally include, for example, fatty acids, neutral fats, phosphatides, glycolipids, aliphatic alcohols and waxes, terpenes and steroids. The lipids may also optionally be fluorinated, and if fluorinated, it is preferred that the lipids are partially fluorinated and most preferable that they are fluorinated at the portions of the alkyl chains furthest from the polar (hydrophilic) headgroups of the lipids.

Exemplary lipids which may be used to prepare lipid compositions include, for example, fatty acids; lysolipids; oils; phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing biocompatible polymers, such as chitin, hyaluronic acid, polyvinylpyrrolidone or polyethylene glycol (PEG), the latter being also referred to herein as "pegylated lipids", with preferred lipids bearing polymers including DPPE-PEG, which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyalkylene sorbitan fatty acid esters (such as, for example, the class of compounds referred to as TWEEN™, commercially available from ICI Americas, Inc., Wilmington, Del.), including polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers and polyoxyethylene fatty acid stearates; sterol aliphatic acid esters, including cholesterol sulfate, cholesterol butyrate, cholesterol iso-butyrate, cholesterol palmitate, cholesterol stearate, lanosterol acetate, ergosterol palmitate and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate and ergosterol gluconate; esters of sugar acids and alcohols including lauryl glucuronide, stearoyl glucuronide, myristoyl glucuronide, lauryl gluconate, myristoyl gluconate and stearoyl gluconate; esters of sugars and aliphatic acids, including sucrose laurate, fructose laurate, sucrose palmitate, sucrose stearate, glucuronic acid, gluconic acid and polyuronic acid; saponins, including sarsasapogenin, smilagenin, hederagenin, oleanolic acid and digitoxigenin; glycerols, including glycerol dilaurate, glycerol trilaurate, glycerol dipalmitate, glycerol and glycerol esters, such as glycerol tripalmitate, glycerol distearate, glycerol tristearate, glycerol dimyristate and glycerol trimyristate; long chain alcohols, including n-decyl alcohol, lauryl alcohol, myristyl alcohol, cetyl alcohol and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy) hexyl-6-amino-6-deoxyl-1-thio-α-D-mannopyranoside; 12-(((7'-diethylaminocoumarin-3-yl)carbonyl)methylamino)-octadecanoic acid; N-[12-(((7'-diethylaminocoumarin-3-yl) carbonyl)methylamino)-octadecanoyl]-2-aminopalmitic acid; cholesteryl)4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

Wall forming and non-vesicular stabilizing materials may optionally be polymerized, thus creating a stable, impermeable shell surrounding the gaseous precursor or otherwise incorporated into the composition. Materials used for this purpose are generally amphiphilic and contain polymerizable groups. Examples include unsaturated lipophilic chains such as alkenyl or alkynyl, containing up to about 50 carbon atoms. Further examples are phospholipids such as phosphoglycerides and sphingolipids carrying polymerizable groups; and saturated and unsaturated fatty acid derivatives with hydroxyl groups, such as for example triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Exemplary polymerizable lipid compounds which may be utilized in the compositions of the present invention are illustrated below.

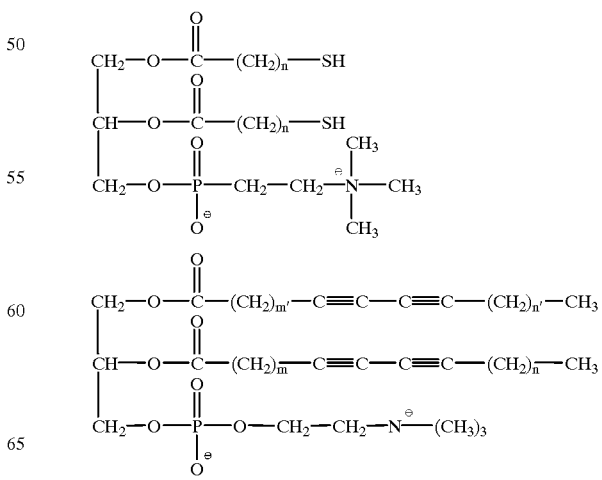

-continued

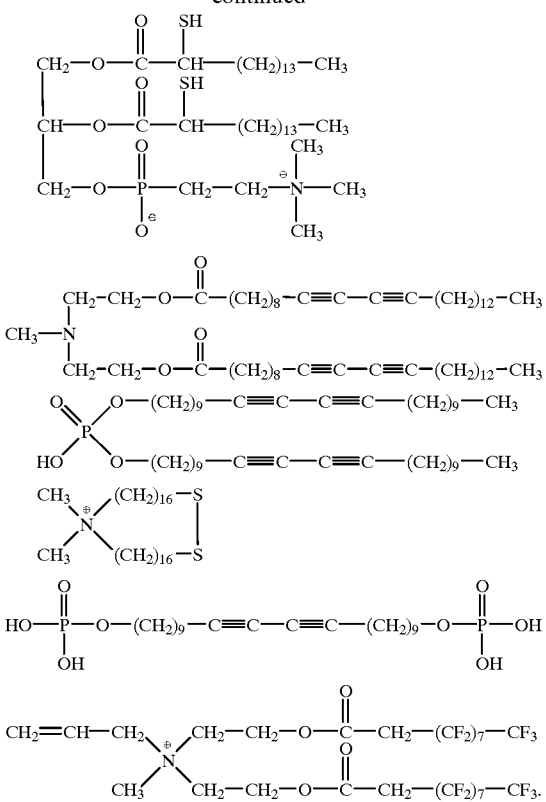

Amphipathic lipids, i.e. lipids containing both a hydrophobic and a hydrophilic domain and capable of forming lamellar structures, are particularly preferred materials for forming the walls and vesicles of the present invention, as well as in non-vesicular compositions. Of these, phospholipids are preferred lipids, particularly for use as wall-forming stabilizing materials in the present invention. Phospholipids may be saturated, monounsaturated, polyunsaturated, or contain mixed chains such as, for example, one saturated chain and one unsaturated chain. More preferred are phospholipids having alkyl chains of from about 14 to about 22 carbon atoms, and most preferred are phospholipids having alkyl chains of from about 16 carbon atoms to about 20 carbon atoms. A particularly preferred phospholipid is dipalmitoylphosphatidylcholine (DPPC).

The lipid materials used in certain of the compositions described herein, especially in connection with vesicle compositions based on lipids, are preferably flexible. This means that, for example, in the case of vesicle compositions based on lipids, the vesicles can alter their shape, for example, to pass through an opening having a diameter that is smaller than the diameter of the vesicle.

If desired, a cationic lipid may be used, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

In the case of lipid compositions which contain both cationic and non-cationic lipids, a wide variety of lipids may be employed as the non-cationic lipid. Preferably, this non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates and alkyl phosphites, may also be used in the lipid compositions.

Saturated and unsaturated fatty acids may also be employed in the lipid compositions described herein and such saturated and unsaturated fatty acids preferably contain from about 12 carbons to about 22 carbons, in linear or branched form. Hydrocarbon groups consisting of isoprenoid units and/or prenyl groups can be used as well. Examples of saturated fatty acids that are suitable include, for example, lauric, myristic, palmitic and stearic acids. Suitable unsaturated fatty acids that may be used include, for example, lauroleic, physeteric, myristoleic, linoleic, linolenic, palmitoleic, petroselinic and oleic acids. Examples of branched fatty acids that may be used include, for example, isolauric, isomyristic, isopalmitic and isostearic acids.

Preferably, the lipids employed in the present invention have a gel to liquid crystalline phase transition temperature at or below the phase transition temperature of the gaseous precursor.

If desired, aggregates may be constructed of one or more charged lipids in association with one or more polymer bearing lipids, optionally in association with one or more neutral lipids. The charged lipids may either be anionic or cationic. Typically, the lipids are aggregated in the presence of a multivalent species, such as a counter ion, opposite in charge to the charged lipid. For delivery of bioactive agents to selective sites in vivo, aggregates of preferably under 2 microns, more preferably under 0.5 microns, and even more preferably under 200 nm are desired. Most preferably the lipid aggregates are under 200 nm in size and may be as small as 5–10 nm in size.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

When the charged lipid is anionic, a multivalent (divalent, trivalent, etc.) cationic material may be used to form aggregates. Useful cations include, for example, cations derived from alkaline earth metals, such as berylium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($pb^{+2}$ and $Pb^{+4}$); transition metals such as titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). It is contemplated that cations in all of their ordinary valence states will be suitable for forming aggregates and cross-linked lipids. Preferred cations include calcium ($Ca^{+2}$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). As will be apparent to one skilled in the art, some of the above ions (notably lead and nickel) may have associated toxicity and thus may be inappropriate for in vivo use.

When the charged lipid is cationic, an anionic material, for example, may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1, 4, 7, 10-tetraazocyclododecane-N',N',N'',N'''-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed hereinabove. A preferred cationic lipid for formation of aggregates is N-[1-(2,3-dioleoyloxy)propyl]-N,N,N-trimethylammonium chloride ("DOTMA"). Synthetic cationic lipids may also be used. These include common natural lipids derivatized to contain one or more basic functional groups. Examples of lipids which can be so modified include dimethyldioctadecylammonium bromide, sphinolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoyl-homocystiene.

Specially synthesized cationic lipids also function in the embodiments of the invention. Among these are those disclosed in pending U.S. patent application Ser. No. 08/391,938, the disclosures of which are hereby incorporated herein by reference in their entirety, and include, for example, N,N'-bis (dodecyaminocarbonylmethylene)-N,N'-bis (β-N,N,N-trimethylammoniumethyl-aminocarbonylmethyleneethylenediamine tetraiodide; N,N''-bis hexadecylaminocarbonylmethylene)-N,N',N''-tris (β-N,N,N-trimethylammonium-ethylaminocarbonylmethylenediethylenetriamine hexaiodide; N,N'-Bis(dodecylaminocarbonylmethylene)-N,N''-bis (β-N,N,N-trimethylammoniumethylaminocarbonylmethylene) cyclohexylene-1,4-diamine tetraiodide; 1,1,7,7-tetra-(β3-N,N,N,N-tetramethylammoniumethylaminocarbonylmethylene)-3-hexadecylaminocarbonyl-methylene-1,3,7-triaazaheptane heptaiodide; and N,N,N'N'-tetra phosphoethanolaminocarbonylmethylene) diethylenetriamine tetraiodide. Those of skill in the art will recognize, once armed with the present disclosure, that other natural and synthetic variants carrying positive charged moieties will also function in the invention.

In addition to lipid compositions and vesicle compositions formulated from lipids, the methods of the present invention may also involve compositions and vesicles formulated from proteins or derivatives thereof. Compositions and vesicles which are formulated from proteins and which would be suitable for use in the methods of the present invention are described, for example, in Feinstein, U.S. Pat. Nos. 4,572,203, 4,718,433 and 4,774,958, and Cerny et al., U.S. Pat. No. 4,957,656, the disclosures of which are hereby incorporated herein by reference in their entirety. Other protein-based vesicles and compositions, in addition to those described in the aforementioned patents, would be apparent to one of ordinary skill in the art, once armed with the present disclosure.

In addition to compositions formulated from lipids and/or proteins, the methods of the present invention may also involve compositions and vesicles formulated from polymers. Exemplary natural polymers suitable for use in the present invention include naturally occurring carbohydrates or polysaccharides. Such polysaccharides include, for example, polymers of or formed from arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, agarose, keratan, chondroitan, dermatan, hyaluronic acid, alginic acid, xanthan gum, starch, heparin (including, for example, heparin sulfate or heparitin sulfate), and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable natural polymers include, for example, proteins, such as albumin, and urokinase. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyoxyethylene and polyoxypropylene copolymers, including polyoxyethylene and polyoxypropylene block copolymers, polyoxyalkylene derivatives of polyethylene glycol (such as, for example, the class of compounds referred to as Pluronics™, commercially available from BASF, Parsippany, N.J.), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, lactides, 2-methacryloyloxytrimethylammonium chloride, and polyvinylidene, as well as polyfunctional cross-linking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof. Preferable synthetic polymers include polyacrylic acid, polyethyleneimine, polymethacrylic acid, polymethylmethacrylate, polysiloxane, polydimethylsiloxane, polylactic acid, poly($\epsilon$-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile, polylactide coglycolide polymers (such as poly-d-L-lactide co-glycolide polymers), and nylon. A particularly preferred copolymer is polyvinylidene-polyacrylonitrile. Other suitable biocompatible monomers and polymers will be readily apparent to those skilled in the art, once armed with the present disclosure. The polymers may optionally be cross-linked, if desired, to enhance, for example, the stability of the vesicle walls.

Methods for the preparation of compositions and vesicles comprising polymers will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference in their entirety.

As an alternative to conventional chemical cross-linking or polymerization, monomers, oligomers, or polymers may be bound together through the use of ionic bonds. For example, vesicles comprising alginic acid may be prepared by "cross-linking" (i.e., creating an ionic or salt bridge) with calcium. As skilled artisans will recognize once armed with the present disclosure, a variety of charged materials may be similarly stabilized into vesicles through the use of an oppositely charged cation or anion which is divalent or of higher valency.

Vesicles derived from lipids, proteins, polymers, etc. for use in the methods of the present invention are preferably low density. The term "low density" refers to vesicles which have an internal void (cavity) volume which is at least about 75% of the total volume of the vesicle. Preferably, the vesicles have a void volume of at least about 80%, more preferably at least about 85%, even more preferably at least about 90%, still more preferably at least about 95%, and yet more preferably about 100% of the total volume of the vesicles.

Gaseous precursors for use in the present invention, when associated with a stabilizing material, may be approximately in the form of droplets or other suitable form. When the stabilizing material is capable of forming walls, the droplets may be in the form of vesicles. While it is not intended that the invention be bound by any theory, it is believed that the expansion of the gaseous precursor during the liquid-to-gas phase transition acts to mechanically induce the release of any bioactive agent from the droplet or vesicle in which it is contained. It will further be recognized that, during the phase transition, the diameter of the droplet, vesicle, etc. will increase. The initial diameter of the droplets, vesicles, etc., meaning the diameter of the droplets, vesicles, etc., containing the gaseous precursor before the gaseous precursor undergoes a phase transition to a gas, may range from about 3 nanometers (nm) to about 10 micrometers ($\mu$m). For purposes of the present invention, the droplets or vesicles may be referred to as "nanodroplets" or "microdroplets" respectively. Preferably, droplets or vesicles for use in the present invention have an initial diameter of from about 30 nm to about 3 $\mu$m, more preferably from about 50 nm to about 2 $\mu$m, and most preferably from about 75 nm to about 1 $\mu$m. The initial diameter of the droplets or vesicles may be chosen for a particular application, for example for diagnostic or therapeutic use in a particular type of tissue or a particular region of a patient. The size may be adjusted, if desired, by procedures including, for example, shaking, microemulsification, vortexing, extrusion, filtration, sonication, homogenization, repeated freezing and thawing cycles, extrusion under pressure through pores of defined size, and similar methods, discussed more fully herein.

In certain embodiments, it may be desirable to use a fluorinated compound, including a perfluorinated compound, which may be in liquid or solid state as stabilizing agents (alone or in addition to other stabilizing agents) to enhance the stability of the gaseous precursor, bioactive agent compositions. Suitable fluorinated compounds include, for example, fluorinated surfactants, including alkyl surfactants, and amphiphilic compounds. A wide variety of such compounds may be employed, including, for example, the class of compounds which are commercially available as ZONYL® fluorosurfactants (the DuPont Company, Wilmington, DE), including the ZONYL® phosphate salts and ZONYL® sulfate salts, which have terminal phosphate or sulfate groups. Representative compounds are disclosed, for example, in U.S. Pat. No. 5,276,145, the disclosures of which are hereby incorporated herein by reference in its entirety. Suitable ZONYL® surfactants also include, for example, ZONYL® surfactants identified as Telomer B, including Telomer B surfactants which are pegylated (i.e., have at least one polyethylene glycol group attached thereto), also known as PEG-Telomer B, available from the DuPont Company. Also suitable are liquid perfluorocarbons, such as for example, perfluorooctylbromide (PFOB), perfluorodecalin, perfluorododecalin, perfluorooctyliodide, perfluorotripopylamine, and perfluorotributylamine, as well as fluorine containing carbohydrates such as those disclosed in Quay, European Patent Application, EPA 0727225, the disclosures of which are hereby incorporated herein by reference in their entirety. In general, perfluorocarbons comprising about six or more carbon atoms will be liquids at normal human body temperature. Among these perfluorocarbons, perfluorooctylbromide and perfluorohexane, which are liquids at room temperature, are preferred. Although not intending to be bound by any theory or theories of operation, it is believed that, especially in the case of vesicle compositions, the liquid fluorinated compound may be situated at the interface between the gaseous precursor and the membrane or wall surface of the vesicle. There may be thus formed a further stabilizing layer of liquid fluorinated compound on the internal surface of the stabilizing compound, for example, a biocompatible lipid used to form the vesicle.

The term "stable" or "stabilized", as used herein with regard to vesicles, means that the vesicles may be substantially resistant to degradation, including, for example, loss of vesicle structure or of encapsulated or entrapped gaseous precursor or bioactive agent, for a useful period of time, e.g., until such release is desired. Typically, the vesicles employed in the present invention have a desirable shelf life, often retaining at least about 90% by volume of its original structure for a period of at least about two to three weeks under normal ambient conditions, although such long shelf life is not required for the present invention. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein may also be stable even under adverse conditions.

The stability of the vesicles described herein may be attributable, at least in part, to the materials from which the vesicles are made, including, for example, the lipids, polymers and proteins described above, and it is often not necessary to employ additional stabilizing materials, although it is optional and may be preferred to do so. Such additional stabilizing materials and their characteristics are described more fully hereinafter.

In addition to, or instead of, the lipid, proteinaceous, polymeric, etc. compounds discussed above, the compositions described herein may comprise one or more additional or basic stabilizing materials. Exemplary of such stabilizing materials are, for example, other biocompatible polymers. The stabilizing materials may be employed to desirably assist in the formation of vesicles or to assure substantial encapsulation of the gases precursors and bioactive agents. These stabilizing materials may help improve the stability and the integrity of the vesicles with regard to their size, shape and/or other attributes.

Particularly preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanolamine-polyethylene glycol 5000 (DSPE-PEG5000).

The vesicle compositions may be prepared from other materials, in addition to the materials described above, provided that the vesicles so prepared meet the stability and other criteria set forth herein. These materials may be basic and fundamental, and form the primary basis for creating or establishing the stabilized gaseous precursor filled vesicles. On the other hand, they may be auxiliary, and act as subsidiary or supplementary agents which can enhance the functioning of the basic stabilizing material or materials, or contribute some desired property in addition to that afforded by the basic stabilizing material. As an example of how basic and auxiliary materials may function, it has been observed that the simple combination of a biocompatible lipid and water or saline when shaken will often give a cloudy solution subsequent to autoclaving for sterilization. In some applications, cloudy solutions may be undesirable; for example such a cloudy solution may imply instability in the form of undissolved or undispersed lipid particles. Such solutions may be undesirable because, for example, manufacturing steps such as sterile filtration may be problematic with solutions containing undissolved particulate matter. Thus, propylene glycol may be added to remove the cloudiness by facilitating dispersion or dissolution of the lipid particles. The propylene glycol may also function as a wetting agent which may improve vesicle formation and stabilization by increasing the surface tension on the vesicle membrane or skin. It is possible that the propylene glycol can also function as an additional layer that may coat a membrane of the vesicle, thus also providing stabilization. Other examples of such further basic or auxiliary stabilizing materials include conventional surfactants, described, for example, in D'Arrigo, U.S. Pat. Nos. 4,684,479 and 5,215,680, the disclosures of which are hereby incorporated herein by reference in their entirety.

Additional auxiliary and basic stabilizing materials include such agents as peanut oil, canola oil, olive oil, safflower oil, corn oil, soybean oil, or any other oil commonly known to be ingestible which is suitable for use as a stabilizing compound in accordance with the teachings herein. Indeed, these oils may be useful for maintaining hydrophobic drugs within vesicular systems. Various auxiliary and basic stabilizing materials are disclosed, for example, in U.S. application Ser. No. 08/444,574, filed May 19, 1995, the disclosures of which is incorporated herein by reference, in their entirety.

In addition, compounds used to make mixed micelle systems may be suitable for use as basic or auxiliary stabilizing materials, and these include, for example, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16'}$), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has also been found that the gaseous precursor-filled vesicles and stabilizing materials used in the present invention may be controlled according to size, solubility and heat stability by choosing from among the various additional or auxiliary stabilizing materials described herein. The additional or auxiliary materials can affect these parameters of the vesicles, etc., especially vesicles formulated from lipids, not only by their physical interaction with vesicle membranes, but also by their ability to modify the viscosity and surface tension of the surface of the gaseous precursor filled vesicles. Accordingly, the gaseous precursor filled vesicles used in the present invention may, for example, be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (b) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents, including, for example, acacia, agar, alginic acid, aluminum monostearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (d) synthetic suspending agents, such as polyethylene glycol (PEG), polyvinylpyrrolidone (PVP), polyvinylalcohol (PVA), polypropylene glycol (PPG), and polysorbate; and (e) tonicity raising agents which stabilize and add tonicity, including, for example, sorbitol, mannitol, trehalose, sucrose, propylene glycol and glycerol.

A wide variety of methods are available for the preparation of lipid, protein, and/or polymer, etc., compositions, both vesicular and non-vesicular. Included among these methods are, for example, shaking, drying, gas-installation, spray drying, and the like. Suitable methods for preparing vesicle compositions from lipids are described, for example, in Unger et al., U.S. Pat. No. 5,469,854, the disclosure of which is incorporated herein by reference in its entirety.

With particular reference to the preparation of micelle compositions, the following discussion is provided. Micelles may be prepared using any one of a variety of conventional micellar preparatory methods which will be apparent to those skilled in the art. These methods typically involve suspension of one or more lipid compounds in an organic solvent, evaporation of the solvent, resuspension in an aqueous medium, sonication and centrifugation. The foregoing methods, as well as others, are discussed, for example, in Canfield et al., Methods in Enzymology, Vol. 189, pp. 418–422 (1990); El-Gorab et al, Biochem. Biophys. Acta, Vol. 306, pp. 58–66 (1973); Colloidal Surfactant, Shinoda, K., Nakagana, Tamamushi and Isejura, Academic Press, N.Y. (1963) (especially "The Formation of Micelles", Shinoda, Chapter 1, pp. 1–88); Catalysis in Micellar and Macromolecular Systems, Fendler and Fendler, Academic Press, N.Y. (1975). The disclosures of each of the foregoing publications are incorporated by reference herein, in their entirety.

As noted above, the vesicle composition may comprise liposomes. A wide variety of methods are available in connection with the preparation of liposome compositions. Accordingly, the liposomes may be prepared using any one of a variety of conventional liposomal preparatory techniques which will be apparent to those skilled in the art. These techniques include, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., Chemistry and Physics of Lipids, 1990 53, 37–46, the disclosure of which is hereby incorporated herein by reference in its entirety. Suitable freeze-thaw techniques are described, for example, in International Application Serial No. PCT/US89/05040, filed Nov. 8, 1989, the disclosure of which is incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing. This may be achieved, for example, by the use of a mechanical shaking device, such as a Wig-L-Bug™ (Crescent Dental, Lyons, Ill.), a Mixomat (Degussa AG, Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizerm (Microfluidics, Woburn, Mass.) may also be used.

Many liposomal preparatory techniques which may be adapted for use in the preparation of vesicle compositions are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., Biochimica etBiophysicaActa, Vol. 858, pp. 161–168 (1986); Hope et al., Biochimica et BiophysicaActa, Vol. 812, pp. 55–65 (1985); U.S. Pat. No. 4,533,254; Mayhew et al., Methods in Enzymology, Vol. 149, pp. 64–77 (1987); Mayhew et al., Biochimica et Biophysica Acta, Vol 755, pp. 169–74 (1984); Cheng et al, Investigative Radiology, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and Liposome Technology, Gregoriadis, G., ed., Vol. in, pp. 29–31, 51–67 and 79–108 (CRC Press Inc., Boca Raton, Fla. 1984), the disclosures of each of which are hereby incorporated by reference herein, in their entirety.

As discussed hereinabove, droplets and vesicles for use in the present invention, as well as other compositional forms of the invention, may be prepared by agitation. The term "agitating," as used herein, means any motion, such as shaking, of an aqueous solution such that gas may be introduced from the local ambient environment into the aqueous solution. Where lipids are employed, this agitation is preferably conducted at a temperature below the gel to liquid crystalline phase transition temperature of the lipid. The shaking involved in the agitation of the solution is preferably of sufficient force to result in the formation of a composition, including vesicle compositions, and particularly vesicle compositions comprising gaseous precursor filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific Co. (Cerritos, Calif.) shaker table, as well as any of the shaking devices described hereinbefore, with the Capmix (Espe Fabrik Pharmazeutischer Praeparate GMBH & Co., Seefeld, Oberay Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicle compositions. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations may be from about 1000 to about 20,000 per minute. More preferably, the number of reciprocations or oscillations may be from about 2500 to about 8000 per minute, with from about 3300 to about 5000 reciprocations or oscillations per minute being even more preferred. Of course, the number of oscillations may be dependent upon the mass of the contents being agitated. Generally speaking, a larger mass may require fewer oscillations. Another means for producing shaking includes the action of gas emitted under high velocity or pressure.

It will also be understood that preferably, with a larger volume of aqueous solution, the total amount of force may be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in patents and patent applications, U.S. Ser. No. 08/076,239, filed Jun. 11, 1993 (U.S. Pat. No. 5,469,854), U.S. Ser. No. 08/076,250, filed Jun. 11, 1993 (U.S. Pat. No. 5,580,575), U.S. Ser. No. 08/159,687, filed Nov. 30, 1993 (U.S. Pat. No. 5,585,112), U.S. Ser. No. 08/160,232, filed Nov. 30, 1993 (U.S. Pat. No. 5,542,935), U.S. Ser. No. 08/307,305, filed Sep. 16, 1994, the disclosures of which are incorporated herein by reference, in their entirety. Emulsion processes may also be employed in the preparation of compositions in accordance with the present invention. Such emulsification processes are described, for example, in Quay, U.S. Pat. Nos. 5,558,094, 5,558,853, 5,558,854, 5,573,751, the disclosures of which are hereby incorporated herein by reference in their entirety. Spray drying may be also employed to prepare the gaseous precursor filled vesicles. Utilizing this procedure, the lipids may be pre-mixed in an aqueous environment and then spray dried to produce gaseous precursor filled vesicles. The vesicles may be stored under a headspace of a desired gas. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay Germany), using, for example, the techniques disclosed in U.S. application Ser. No. 160,232, filed Nov. 30, 1993, the disclosures of which are hereby incorporated herein by reference in its entirety. In addition, after extrusion and sterilization procedures, which are discussed in detail below, agitation or shaking may provide vesicle compositions which can contain substantially no or minimal residual anhydrous lipid phase in the remainder of the solution. (Bangham, A. D., Standish, M. M, & Watkins, J. C., J. Mol. Biol. Vol. 13, pp. 238–252 (1965). Other preparatory techniques include those described in Unger, U.S. Pat. No. 5,205,290, the disclosures of which are hereby incorporated herein by reference in their entirety.

The size of gaseous precursor filled vesicles can be adjusted, if desired, by a variety of procedures, including, for example, microemulsification, vortexing, extrusion, filtration, sonication, spray drying, homogenization, repeated freezing and thawing cycles, extrusion under pressure through pores of defined size, and similar methods. Gaseous precursor filled vesicles prepared in accordance with the methods described herein can range in size from less than about 1 $\mu$m to greater than about 100 $\mu$m. In addition, after extrusion and sterilization procedures, which are discussed in detail below, agitation or shaking may provide vesicle compositions which can contain substantially no or minimal residual anhydrous lipid phase in the remainder of the solution. (Bangham, A. D., Standish, M. M, & Watkins, J. C., J. Mol. Biol. Vol. 13, pp. 238–252 (1965). If desired, the vesicles may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles may be significantly smaller, for example, less than about 100 nm in diameter. For enteric or gastrointestinal use, the vesicles may be significantly larger, for example, up to a millimeter in size. Preferably, the vesicles may have diameters of from about 2 $\mu$m to about 100 $\mu$m. Determination of the size of the droplets may be accomplished by, for example, quasielastic light scattering or optical microscopy.

The gaseous precursor filled vesicles may be sized by a simple process of extrusion through filters wherein the filter pore sizes control the size distribution of the resulting gaseous precursor filled vesicles. By using two or more cascaded or stacked set of filters, for example, a 10 $\mu$m filter followed by an 8 $\mu$m filter, the gaseous precursor filled vesicles can be selected to have a very narrow size distribution around 7 to 9 $\mu$m. After filtration, these gaseous precursor filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and may be carried out by a step of extracting which comprises extruding the vesicles from the barrel through the filter fitted to the syringe between the barrel and the needle, thereby sizing the vesicles before they are administered to a patient. The step of extracting may also comprise drawing the vesicles into the syringe, where the filter may function in the same way to size the vesicles upon entrance into the syringe. Another alternative is to fill such a syringe with vesicles which have already been sized by some other means, in which case the filter may function to ensure that only vesicles within the desired size range, or of a desired maximum size, are subsequently administered by extrusion from the syringe.

In certain preferred embodiments, the vesicle compositions may be heat sterilized or filter sterilized and extruded through a filter prior to shaking. Generally speaking, vesicle compositions comprising gaseous precursors are preferably filter sterilized. Once gaseous precursor filled vesicles are formed, they may be filtered for sizing as described above. Performing these steps prior to the formation of gaseous precursor filled vesicles can provide sterile gaseous precursor filled vesicles ready for administration to a patient. For example, a mixing vessel such as a vial or syringe may be filled with a filtered lipid, etc. and/or vesicle composition, and the composition may be sterilized within the mixing vessel, for example, by autoclaving. Preferably, the sterile vessel is equipped with a filter positioned such that the gaseous precursor filled vesicles pass through the filter before contacting a patient.

The step of extruding the solution of lipid, etc. compound through a filter decreases the amount of unhydrated material by breaking up any dried materials and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, which is generally undesirable, appears as amorphous clumps of non-uniform size.

The sterilization step provides a composition that may be readily administered to a patient. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

The present invention utilizes gaseous precursors, in droplets or vesicles, which, upon exposure to temperatures above normal body temperature, form a gas. This process is described in detail in copending patent applications Ser. Nos. 08/160,232, filed Nov. 30, 1993 and 08/159,687, filed Nov. 30, 1993, the disclosures of which are incorporated herein by reference, in their entirety.

The preferred method of activating the gaseous precursor is by exposure to elevated body temperature. Activation or transition temperature, and like terms, refer to the boiling point of the gaseous precursor, which is the temperature at which the phase transition of the gaseous precursor from a solid or liquid to a gas takes place. As discussed hereinabove, useful gaseous precursors are those materials which have boiling points in the range of about 36° C. to about 56° C. The activation temperature is particular to each gaseous precursor. An activation temperature of above about 37° C., or above about human body temperature, is preferred for gaseous precursors in the context of the present invention. Thus, in preferred form, a liquid gaseous precursor is activated to become a gas at above about 37° C. The gaseous precursor may thus be selected so as to form the gas in situ in the targeted tissue or fluid, according to its transition temperature.

The methods of preparing the gaseous precursor filled vesicles are preferably carried out below the boiling point of the gaseous precursor so that a liquid is incorporated, for example, into a vesicle. Thus, the gaseous precursor may be entrapped within a vesicle so that the liquid-to-gas phase transition does not occur during manufacture, and the gaseous precursor filled vesicles are manufactured in the liquid phase of the gaseous precursor. For gaseous precursors having low temperature boiling points, liquid precursors may be emulsified using a microfluidizer device chilled to a low temperature. The boiling points may also be depressed using solvents in liquid media to utilize a precursor in liquid form. However, as discussed herein, because the present invention relates to the delivery of gaseous precursors to targeted tissue, where the gaseous precursors preferably form a gas, it is generally preferable to utilize gaseous precursors which are liquid, or solid, at storage and manufacturing temperature. Activation of the phase transition may take place at any time as the temperature is allowed to exceed the boiling point of the precursor.

As a further embodiment of this invention, by preforming the gaseous precursor in the liquid state into an aqueous emulsion, and knowing the amount of gaseous precursor contained in a vesicle, the maximum size of the vesicle may be estimated by using the ideal gas law, once the transition to the gaseous state is effectuated. For the purpose of generating gas filled vesicles from gaseous precursors, the gas phase may be assumed to form instantaneously and it may be assumed that substantially no gas in the newly formed vesicle has been depleted due to diffusion into the liquid, which is generally aqueous in nature. Hence, from a known liquid volume in the emulsion, one may predict an upper limit to the size of the gas filled vesicle.

The ideal gas law, which can be used for calculating the increase in the volume of the gas bubbles upon transitioning from liquid to gaseous states, is as follows:

$$PV = nRT$$

where

P is pressure in atmospheres (atm);

V is volume in liters (L);

n is moles of gas;

T is temperature in degrees Kelvin (K); and

R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, may expand into a vesicle of known volume. The calculated volume may reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation:

$$\text{Volume (spherical vesicle)} = 4/3 \, \pi r^3$$

where r is the radius of the sphere.

Thus, once the volume is predicted, and knowing the density of the liquid at the desired temperature, the amount of liquid gaseous precursor in the droplet may be determined. In more descriptive terms, the following can be applied:

$$V_{gas} = \tfrac{4}{3}\pi(r_{gas})^3$$

by the ideal gas law, $$PV = nRT$$

substituting reveals, $$V_{gas} = nRT/P_{gas}$$

or, (A) $n = \tfrac{4}{3}[\pi r_{gas}^3]P/RT$ amount $n = \tfrac{4}{3}[\pi r_{gas}^3 P/RT]\cdot MW_n$ Converting back to a liquid volume (B) $V_{liq} = [\tfrac{4}{3}[\pi r_{gas}^3]P/RT]\cdot MW_n/D]$ where D is the density of the precursor.

Solving for the diameter of the liquid droplet, (C) $\text{diameter}/2 = [\tfrac{3}{4}\pi[\tfrac{3}{4}\cdot[\pi r_{gas}^3]P/RT]MW_n/D]]^{1/3}$ which reduces to $\text{Diameter} = 2[[r_{gas}^3]P/RT\,[MW_n/D]]^{1/3}$.

In embodiments of the present invention, a mixture of a lipid compound and a gaseous precursor, for example, containing liquid droplets of defined size, may be formulated such that upon reaching a specific temperature, for example, the boiling point of the gaseous precursor, the droplets may expand into gas filled vesicles of defined size. The defined size may represent an upper limit to the actual size because the ideal gas law generally cannot account for such factors as gas diffusion into solution, loss of gas to the atmosphere, and the effects of increased pressure.

A representative gaseous precursor may be used to form a vesicle of defined size, for example, 10 µm diameter. In this example, the vesicle may be formed in the bloodstream of a human being, thus the typical temperature would be 37° C. or 310 K. At a pressure of 1 atmosphere and using the equation in (A), $7.54 \times 10^{-17}$ moles of gaseous precursor may be required to fill the volume of a 10 µm diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor may be required for a 10 µm vesicle. Extrapolating further, and with the knowledge of the density, equation (B) further predicts that $8.47 \times 10^{-16}$ mL of liquid precursor may be necessary to form a vesicle with an upper limit of 10 µm.

Finally, using equation (C), a mixture, for example, an emulsion containing droplets with a radius of 0.0272 µm or a corresponding diameter of 0.0544 µm, may be formed to make a gaseous precursor filled vesicle with an upper limit of a 10 µm vesicle.

An emulsion of this particular size could be easily achieved by the use of an appropriately sized filter. In addition, as seen by the size of the filter necessary to form gaseous precursor droplets of defined size, the size of the filter may also suffice to remove any possible bacterial contaminants and, hence, can be used as a sterile filtration as well.

The selection of appropriate solvent systems may be determined by physical methods as well. When substances, solid or liquid, herein referred to as solutes, are dissolved in a solvent, such as water based buffers, the freezing point may be lowered by an amount that is dependent upon the composition of the solution. Thus, as defined by Wall, one can express the freezing point depression of the solvent by the following equation:

$$\ln x_a = \ln(1-x_b) = \Delta H_{fus}/R(1T_o - 1/T)$$

where $x_a$ is the mole fraction of the solvent;

$x_b$ is the mole fraction of the solute;

$\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as follows.

$$X_b = \Delta H_{fus}/R[T - T_o/T_oT] = \Delta H_{fus}\Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m + 1000/m_a] = mMa/1000$$

where $M_a$ is the molecular weight of the solvent.

Thus, substituting for the fraction $x_b$:

$$\Delta T = [M_aRT_o^2/1000\Delta H_{fus}]m$$

or $$\Delta T = K_f m, \text{ where}$$

$$K_f = M_aRT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles (as well as non-vesicular formulations) include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 µm. Alternatively, filtering may be performed during in vivo administration of the vesicles such that a filter of about 0.22 µm is employed;

(b) microemulsification, whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles may float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying may be useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

As discussed hereinabove, preferred methods for preparing the temperature activated gaseous precursor filled vesicles comprise shaking an aqueous solution comprising a lipid compound in the presence of a gaseous precursor at a temperature below the phase transition temperature of the gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined.

As noted above, the non-vesicular and/or vesicle compositions may be sterilized by autoclave or sterile filtration if these processes are performed before the installation step or prior to temperature mediated conversion of the temperature sensitive gaseous precursors within the compositions. Alternatively, one or more anti-bactericidal agents and/or preservatives may be included in the formulation of the compositions, such as sodium benzoate, quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, may be necessary where the stabilized vesicles are used for imaging under invasive circumstances, for example, intravascular or intraperitoneal. The appropriate means of sterilization will be apparent to the artisan based on the present disclosure.

Vesicle compositions which comprise vesicles formulated from proteins (also referred to as protein encapsulated microbubbles), such as albumin vesicles, may be prepared by various conventional processes, as can non-vesicular protein compositions, as will be readily apparent to those skilled in the art, once armed with the present disclosure. Suitable methods include those described, for example, in Feinstein, U.S. Pat. Nos. 4,572,203, 4,718,433 and 4,774,958, and Cerny et al., U.S. Pat. No. 4,957,656, the disclosures of which are hereby incorporated herein by reference, in their entirety. Included among the methods described in the aforementioned patents for the preparation of protein-based vesicles and non-vesicular compositions are methods which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, collagen, and the like. Preferably, the protein is a human protein, with human serum albumin (HSA) being more preferred. HSA is available commercially as a sterile 5% aqueous solution, which is suitable for use in the preparation of protein-based vesicles. Of course, as would be apparent to one of ordinary skill in the art, other concentrations of albumin, as well as other proteins which are heat-denaturable, can be used to prepare the vesicles. The concentration of HSA in solution can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

The protein-based vesicles and non-vesicular compositions may be prepared using equipment which is commercially available. For example, in connection with a feed preparation operation as disclosed, for example, in Cerny, et al., U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonicating vessel, in series. Heat exchanger equipment of this type may be obtained from ITT Standard (Buffalo, N.Y.). The heat exchanger maintains operating temperature for the sonication process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commercially available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficient to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from 5 about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a composition having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based compositions may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteraldehyde per gram of protein at pH 4.5 for 6 hours. The unreacted gluteraldehyde may then be washed away from the protein.

Vesicle compositions which comprise vesicles formulated from polymers may be prepared by various conventional processes, as can non-vesicular polymer compositions, as will be readily apparent to those skilled in the art, once armed with the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in Garner et al., U.S. Pat. No. 4,179,546, Garner, U.S. Pat. No. 3,945,956, Cohrs et al., U.S. Pat. No. 4,108,806, Japan Kokai Tokkyo Koho 62 286534, British Patent No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Pat. No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Pharmacology*, Vol 44, pp. 115–129 (1966), and Chang, *Science*, Vol. 146, pp. 524–525 (1964), the disclosures of each of which are incorporated herein by reference in their entirety.

In accordance with a preferred synthesis protocol, the vesicles may be prepared using a heat expansion process, such as, for example, the process described in Garner et al., U.S. Pat. No. 4,179,546, Garner, U.S. Pat. No. 3,945,956, Cohrs et al., U.S. Pat. No. 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticizing the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethyl-methacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2$—$CCl_2F_2$, chloroheptafluorocyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

To incorporate the bioactive agent and gaseous precursor in the composition along with the stabilizing compound, the compositions may be prepared as described above by simply adding the bioactive agent and gaseous precursor during the preparation process. Alternatively, compositions may be preformed first from stabilizing materials and gaseous precursors, and the bioactive agent may be then added to the composition prior to use. For example, an aqueous mixture of liposomes and gaseous precursor may be prepared to which the bioactive agent may be added and which is agitated to provide the liposome formulation. The liposome formulation can be readily isolated by heating the solution thereby causing the gaseous precursor to convert to gas and the filled liposome vesicles float to the top of the aqueous solution. Excess bioactive agent can be recovered from the remaining aqueous solution. Also, vesicles may be made porous or otherwise capable of imbibing the liquid precursor and/or bioactive agent, if desired. Of course, a composition of bioactive agent and gaseous precursor may be formulated without a stabilizing agent by simply mixing the compounds. These, as well as other, preparatory techniques for all of the compositional variations within the scope of the invention will be readily apparent to one skilled in the art, once armed with the present disclosure.

As those skilled in the art will recognize, any of the lipid, protein, polymer, etc. and/or vesicle compositions may be lyophilized for storage, and reconstituted, for example, with an aqueous medium (such as sterile water, phosphate buffered solution, or aqueous saline solution), with the aid of vigorous agitation. To prevent agglutination or fusion of the lipids as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol) (PEG), for example, PEG polymers having a molecular weight of from about 400 to about 10,000, with PEG polymers having molecular weights of about 1000, 3000 (such as PEG3350) and 5000 being preferred. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

As discussed above, the compositions and methods of the present invention are useful for targeting selected tissue, fluid, region, etc. of a patient. Targeting may be for the purpose of delivering a bioactive agent to the desired tissue, fluid, or region. The bioactive agent may be therapeutic, diagnostic, or may be an agent which facilitates or improves diagnostic imaging. Genetic materials and therapeutic agents, also called drugs or pharmaceuticals, may be delivered using the methods of the invention.

Bioactive agents which can be delivered using the methods of the invention thus include, for example, synthetic organic molecules, proteins, peptides, antibiotics, hormones, vitamins, vasoactive compounds, antihelminthics, antimalarial agents, antitoxins, antivenins, anticoagulants, neuromuscular blockers, circulatory drugs, local and general anesthetics, antithrombotics, chemotherapeutic agents, bioactive peptides, genes and anti-sense genetic materials.

Particular examples of pharmaceutical agents which may be delivered by the methods of the present invention include, but are not limited to: mitotic inhibitors such as the vinca alkaloids, radiopharmaceuticals such as radioactive iodine, phosphorus and cobalt isotopes; hormones such as progestins, estrogens and antiestrogens; anti-helminthics, antimalarials and antituberculosis drugs; biologicals such as immune sera, antitoxins and antivenins; rabies prophylaxis products; bacterial vaccines; viral vaccines; aminoglycosides; respiratory products such as xanthine derivatives, theophylline and aminophylline; thyroid therapeutics such as iodine salts and anti-thyroid agents; cardiovascular products including chelating agents and mercurial diuretics and cardiac glycosides; glucagon; blood products such as parenteral iron, hemin, hematoporphyrins and their derivatives; targeting ligands such as peptides, antibodies, and antibody fragments; biological response modifiers such as muramyl dipeptide, muramyl tripeptide, microbial cell wall components, lymphokines (e.g. bacterial endotoxin such as lipopolysaccharide and macrophage activation factor); subunits of bacteria (such as Mycobacteria and Comebacteria); the synthetic dipeptide N-acetyl-muramyl-L-alanyl-D-isoglutamine; antifungal agents such as ketoconazole, nystatin, griseofulvin, flucytosine (5-fc), miconazole, and amphotericin B; toxins such as ricin; immunosuppressants such as cyclosporins; and antibiotics such as β-lactam and sulfazecin; hormones such as growth hormone, melanocyte stimulating hormone, estradiol, beclomethasone dipropionate, betamethasone, betamethasone acetate, betamethasone sodium phosphate, betamethasone disodium phosphate, betamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, and vasopressin, as well as their derivatives; vitamins such as cyanocobalamin neionic acid; retinoids and derivatives such as retinol palmitate and α-tocopherol; peptides and enzymes such as manganese superoxide dismutase and alkaline phosphatase; anti-allergens such as amelexanox; anti-coagulation agents such as phenprocoumon and heparin; tissue plasminogen activators (TPA), streptokinase, and urokinase; circulatory drugs such as propranolol; metabolic potentiators such as glutathione; antibiotics such as p-aminosalicyclic acid, isoniazid, capreomycin sulfate cycloserine, ethambutol hydrochloride ethionamide, pyrazinamide, rifampin, streptomycin sulfate dapsone, chloramphenicol, neomycin, ceflacor, cefadroxil, cephalexin, cephadrine erythromycin, clindamycin, lincomycin, amoxicillin, ampicillin, bacampicillin, carbenicillin, dicloxicillin, cyclacillin, picloxicillin, hetacillin, methicillin, nafcililn, oxacillin, penicillin (G and V), ticarcillin rifampin and tetracycline; antivirals such as acyclovir, DDI, Foscarnet, zidovudine, ribavirin and vidarabine monohydrate; antianginals such as diliazem, nifedipine, verapamil, erythritol tetranitrate, isosorbide dinitrate, nitroglycerin (glyceryl trinitrate) and pentaerythritol tetranitrate; antiinflammatories such as difluisal, ibuprofin, indomethacin, meclofenamate, mefenamic acid, naproxen, oxyphenbutazone, phenylbutazone, piroxicam, sulindac, tolmetin, aspirin, and salicylates; antiprotozoans such as chloraquine, hydroxychloraquine, metranidazole, quinine and meglumine antimonate; antirheumatics such as penicillamine; narcotics such as paregoric; opiates such as codeine, heroin, methadone, morphine, and opium; cardiac glycosides such as deslanoside, digitoxin, digoxin, digitalin, and digitalis; neuromuscular blockers such as atracurium nesylate, gallamine triethiodide, hexaflorenium bromide, metrocurine iodide, pancurium bromide, succinylcholine chloride (suxamethonium chloride), tubocurarine chloride and vecuronium bromide; sedatives such as amorbarital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, secobarbital sodium, tulbutal, temazepam and trizolam; local anesthetics such as bupivacaine hydrochloride, chloroprocaine hydrochloride, etidocaine hydrochloride, lidocaine hydrochloride, mepivacaine hydrochloride, procaine hydrochloride, and tetracaine hydrochloride; general anaesthetics such as droperidol, etamine hydrochloride, methohexital sodium and thiopental sodium; antineoplastic agents such as methotrexate, fluorouracil, adriamycin, mitomycin, ansamitomycin, bleomycin, cystein arabinoside, arabinosyl adenine, mercaptopolylysine, vincristine, busulfan, chlorambucil, azidothymidine, melphalan (e.g. PAM, L-PAM or phenylalanine mustard), mercaptopurine, mitotane, procarbazine hydrochloride dactinomycin (actinomycin D), danorubicin hydrochloride, dosorubicin hydrochloride, taxol, plicamycin (mithramycin), aminoglutethimide, estramustine phosphate sodium, flutamide, leuprolide acetate, leuprolide acetate, megestrol acetate, tamoxifen citrate, testolactone, trilostane, amsacrine (m-AMSA), asparaginase, etoposide (VP-16), interferon α-2a, interferon α-2b, teniposide (VM-26), vinblastine sulfate (VLB), vincristine sulfate, hydroxyurea, procarbaxine, and dacarbazine.

Diagnostic agents include any of a wide variety of agents useful in facilitating or improving diagnostic imaging, such as any of the many contrast agents used in ultrasound imaging, magnetic resonance imaging, computed tomography imaging and the like. Diagnostic agents may also include any other agents useful in facilitating diagnosis of a disease or other condition in a patient, whether or not imaging methodology is employed. Such agents will be well known to those skilled in the art.

To practice the invention, one or more bioactive agents may be incorporated into the lipid, protein, or polymer composition, or vesicle, containing the gaseous precursor. As noted above, the bioactive agent may be readily incorporated when it is soluble in the gaseous precursor by agitating the gaseous precursor and bioactive agent and then extruding to prepare suitably sized gaseous precursor/bioactive agent droplets. Agitation may be accomplished by conventional methods such as, for example, sonication, vortexing, microfluidization, or shaking.

It is preferred that the bioactive agent to be delivered to a region or tissue be soluble in the gaseous precursor. However, if the bioactive agent is insoluble in the gaseous precursor, the bioactive agent may be derivatized to increase its solubility in the gaseous precursor. Derivatized therapeutics can, for example, be dissolved in oils or other biocompatible non-polar solvents. It will be understood by one skilled in the art that any means of derivitization which does not adversely affect the activity of the bioactive agent at delivery will be suitable. Alternatively, the bioactive agent may be derivatized to form a derivative which will become stabilized at or near the stabilizing and/or wall-forming material.

Bioactive agents which are not soluble in the gaseous precursor and not derivatized may be used in the method of the invention. For example, certain bioactive agents which are insoluble in the gaseous precursor may form crystals, which may become associated with the stabilizing and/or wall-forming material. The crystals may be emulsified to improve their dispersion within the gaseous precursor.

Certain bioactive agents will also form an affinity with the stabilizing material. These bioactive agents may become associated with the walls or surfaces of gaseous precursor-filled droplets. For example, DNA may become associated with cationic lipids or cationic polymers.

The delivery of the bioactive agent to a desired tissue or region of the body is activated when the local temperature is at or above the phase transition temperature of the gaseous precursor. As the vesicle or non-vesicular composition or formulation containing the gaseous precursor circulates through the patient's body, it will pass through tissues via the vasculature. As the gaseous precursor passes through a tissue or region which is at the phase transition temperature of the gaseous precursor, it will undergo transition to a gaseous state. While not intending to be bound by any particular theory of operation, it is believed that the expansion of the gaseous precursor during the phase transition forces the bioactive agent from the vesicle or non-vesicular composition allowing it to settle in the desired region of the patient. In a preferred embodiment of the invention, the delivery of a bioactive agent is accomplished simply due to the increase in temperature in a tissue or region associated with disease, infection, inflammation, etc. within the tissue or region.

Preferably, the gaseous precursor forms a gas at the desired tissue or region of the body, which may be at an elevated temperature as compared to the normal body temperature, due to disease, infection, inflammation, etc.. However, external heat (i.e., heat from a source other than the elevated physiological temperatures of the region) also may be applied to increase the temperature within a region or tissue of a patient, if desired. External heat may be applied by any means known in the art, such as, for example, microwave, radiofrequency, ultrasound, and other local application of heat. Local application of heat may be accomplished, for example, by a water bath or blankets. A temperature increase in a desired tissue or region of the body may be achieved by implantation of interstitial probes or insertion of a catheter, in combination with the application of an oscillating magnetic field or ultrasound energy. If ultrasound energy is used, the ultrasound energy may also interact with the gaseous precursor and/or stabilizing material, and may facilitate conversion of the gaseous precursor to a gas and/or release of a bioactive agent. As will be apparent to those skilled in the art, applied ultrasound energy may be pulsed, swept, or varied to facilitate interaction with the gaseous precursor and stabilizing material. Diagnostic ultrasound may be used in order to visualize the gaseous precursors as the gas is formed, and to visualize the tissue or region of interest.

As one skilled in the art will recognize, administration of the lipid and/or vesicle compositions described herein can be carried out in various fashions, including parenterally, orally, or intraperitoneally. Parenteral administration, which is preferred, includes administration by the following routes: intravenous; intramuscular; interstitially; intra-arterially; subcutaneous; intraocular; intrasynovial; transepithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration. The useful dosage to be administered and the particular mode of administration will vary depending upon the age, weight and the particular mammal and region thereof to be scanned, and the particular contrast agent employed. Typically, dosage is initiated at lower levels and increased until the desired contrast enhancement is achieved. Various combinations of the lipid compositions may be used to alter properties as desired, including viscosity, osmolarity or palatability. In carrying out the embodiments of the present invention which involve imaging, the bioactive can be used alone, or in combination with diagnostic, therapeutic or other agents. Such other agents include excipients such as flavoring or coloring materials.

In the case of diagnostic applications, such as ultrasound imaging, magnetic resonance imaging and computed tomography imaging, energy, such as ultrasonic energy (in the case of ultrasound imaging), may be applied to at least a portion of the patient to image the target tissue. A visible image of an internal region of the patient, or other useful data readout or image, may be then obtained, such that the presence or absence of diseased tissue can be ascertained. With respect to ultrasound, ultrasonic imaging techniques, including but not limited to second harmonic imaging and gated imaging, are well known in the art, and are described, for example, in Uhlendorf, "Physics of Ultrasound Contrast Imaging: Scattering in the Linear Range", *IEEE Transactions on Ultrasonics, Ferroelectrics, and Frequency Control,* Vol. 14(1), pp. 70–79 (1994) and Sutherland, et al., "Color Doppler Myocardial Imaging: A New Technique for the Assessment of Myocardial Function", *Journal of the American Society of Echocardiography,* Vol. 7(5), pp. 441–458 (1994), the disclosures of which are hereby incorporated herein by reference in their entirety. Computed tomography imaging techniques which may be employed are conventional and are described, for example, in Computed Body Tomography, Lee, J. K. T., Sagel, S. S., and Stanley, R. J., eds., 1983, Ravens Press, New York, N.Y., especially the first two chapters thereof entitled "*Physical Principles and Instrumentation*", TerPogossian, M. M., and "*Techniques*", Aronberg, D. J., the disclosures of which are hereby incorporated by reference herein in their entirety. Magnetic resonance imaging techniques are described, for example, in D. M. Kean and M. A. Smith, *Magnetic Resonance Imaging: Principles and Applications,* (William and Wilkins, Baltimore, 1986), the disclosures of which are hereby incorporated herein by reference in their entirety. Contemplated magnetic resonance imaging techniques include, but are not limited to nuclear magnetic resonance imaging and electronic spin resonance. These and other diagnostic imaging techniques are well known to those skilled in the art.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency may be received, where x is the incidental frequency. This may serve to decrease the signal from the background material and enhance the signal from the transducer using the targeted contrast media of the present invention which may be targeted to the desired site. Other harmonics signals, such as odd harmonics signals, for example, 3x or 5x, may be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate or cyanomethacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there may be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle species. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%. If it is desired that the vesicles remain intact at normal body temperatures and rupture only at elevated temperatures, the use of higher energy ultrasound is not preferred.

In the case of vesicle compositions formulated from lipids, the concentration of lipid required to form a desired stabilized vesicle level may vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution. The concentration of distearoylphosphatidylcholine (DSPC) used in preferred embodiments may be from about 0.1 mg/mL to about 30 mg/mL of saline solution, more preferably from about 0.5 mg/mL to about 20 mg/mL of saline solution, and even more preferably from about 1 mg/mL to about 10 mg/mL of saline solution. The amount of composition which is administered to a patient can vary. Typically, the intravenous dose may be less than about 10 mL for a 70 Kg patient, with lower doses being preferred.

As noted above, administration of the compositions described herein may be carried out in various fashions, such as intravascularly, orally, rectally, and the like, using a variety of dosage forms. In embodiments of the invention which involve imaging, a region or tissue of interest may be scanned according to desired imaging techniques. When the region to be scanned is the cardiovascular region, administration of the contrast medium is preferably carried out intravascularly. When the region to be scanned is the gastrointestinal region, administration of the contrast medium is preferably carried out orally or rectally. The useful dosage to be administered and the particular mode of administration will vary depending upon the age, weight and the particular mammal and region thereof targeted, and the particular bioactive agent to be delivered. Typically, dosage may be initiated at lower levels and increased until the desired contrast enhancement is achieved. Various combinations of the non-vesicular and vesicle compositions may be used to modify the relaxation behavior of the medium or to alter properties such as the viscosity, osmolarity or palatability (in the case of orally administered materials).

In accordance with certain preferred embodiments of the present invention, the rate at which lipid, protein, polymer, etc. and/or vesicle compositions which comprise a gaseous precursor are administered may be determined and regulated as follows. The compositions may be administered to a patient at a dose of, for example, about 10 microliters ($\mu$L) of composition per kilogram (Kg) of patient body weight (10 $\mu$L/Kg). In certain preferred embodiments, the compositions may contain gaseous precursor in a concentration which provides a dose of gas ranging from about $1 \times 10^{-4}$ to about $5 \times 10^{-3}$ cubic centimeters (cc) of gas per kilogram (Kg) of patient body weight, and all combinations and subcombinations of ranges therein. This gas dose may be employed to provide an administration rate of gas to a patient, referred to herein as the "gas administration rate." The compositions may be administered over a period of time which can vary and depends upon a variety of factors including, for example, the volume of the composition being administered, the age and weight of the patient, the particular materials employed in the compositions, including, for example, lipids, polymers, proteins, vesicles, gases and/or gaseous precursors, the purpose for the administration (for example, diagnostic or therapeutic), the region of interest, the mode of administration, the size of the vesicles (in the case of vesicle compositions), and the like. An exemplary administration time for the compositions described above is about 5 seconds. Dividing the gas dose by this time period provides a gas administration rate which can be expressed as cc gas/Kg-sec. Thus, a gas dose of, for example, about $1 \times 10^{-4}$ cc gas/Kg and an administration time of 5 sec provides a gas administration rate of about $2 \times 10^{-5}$ cc gas/Kg-sec. Alternatively, sustained infusion may be employed.

It is to be understood that the foregoing specific gas concentrations, composition doses, administration times and administration rates are for purposes of illustration only, and not for purposes of limitation.

In connection with preferred embodiments of the invention, the lipid, protein, polymer, etc. and/or vesicle compositions may be administered to a patient to provide a gas administration rate which ranges from about $1 \times 10^{-7}$ to about $3 \times 10^{-3}$ cc gas/Kg-sec, and all combinations and subcombinations of ranges therein including, for example, from about $4 \times 10^{-7}$, $8 \times 10^{-7}$, $1 \times 10^{-4}$, $2 \times 10^{-6}$ or about $3 \times 10^{-6}$ to about $3 \times 10^{-3}$ cc gas/Kg-sec. More preferably, the lipid, protein, polymer and/or vesicle compositions may be administered to provide a gas administration rate of from about $4 \times 10^{-6}$ to about $2 \times 10^{-3}$ cc gas/Kg-sec, with gas administration rates of from about $5 \times 10^{-6}$, $6 \times 10^{-6}$, $7 \times 10^{-6}$ or $8 \times 10^{-6}$ to about $2 \times 10^{-3}$ cc gas/Kg-sec being even more preferred. Still more preferably, the lipid, protein, polymer and/or vesicle compositions may be administered to provide a gas administration rate of from about $9 \times 10^{-6}$ or $1 \times 10^{-5}$ to about $1 \times 10^{-3}$ cc gas/Kg-sec, with gas administration rates of from about $2 \times 10^{-5}$, $3 \times 10^{-5}$, $4 \times 10^{-5}$ or $5 \times 10^{-5}$ to about $1 \times 10^{-3}$ cc gas/Kg-sec being still more preferred. Yet more preferably, the lipid, protein, polymer and/or vesicle compositions may be administered to a patient at a gas administration rate of from about $6 \times 10^{-5}$, $7 \times 10^{-5}$, $8 \times 10^{-5}$ or $9 \times 10^{-5}$ to less than about $1 \times 10^{-3}$ cc gas/Kg-sec, with gas administration rates of from about $1 \times 10^{-4}$ to about $9 \times 10^{-4}$ cc gas/Kg-sec being even still more preferred.

Gaseous precursors incorporated in the compositions described herein may be, for example, liquids or solids, which are converted to a gas after administration (that is, in vivo), in a tissue or region which is at an elevated temperature. As would be apparent to one of ordinary skill in the art, once armed with the present disclosure, concentrations of gaseous precursors may be employed in the compositions, and administration rates of compositions which contain gaseous precursors may be employed, which provide the foregoing gas administration rates upon conversion of the gaseous precursor into a gas.

As noted above, vesicle compositions represent a preferred form of the compositions employed in the methods of the present invention. Also as noted above, the concentration of vesicles in the vesicle compositions is preferably at least about $1.5 \times 10^8$ vesicles per mL of vesicle composition (vesicles/mL), more preferably at least about $1 \times 10^9$ vesicles/mL, and even more preferably at least about $1.5 \times 10^9$ vesicles/mL. This vesicle concentration may be employed to provide an administration rate of vesicles to a patient, referred to herein as the "vesicle administration rate." In this connection, the vesicle compositions may be administered to a patient at a dose of, for example, about 10 microliters ($\mu$L) of vesicle composition per kilogram (Kg) of patient body weight (10 $\mu$L/Kg). The product of the vesicle concentration (vesicles/mL) and the dose of the vesicle composition ($\mu$L/Kg) provides a vesicle dose which can be expressed as vesicles/Kg. Thus, the highly preferred vesicle concentration ($1.5 \times 10^9$ vesicles/mL) and the vesicle composition dose (10 $\mu$L/Kg) described above provides a vesicle dose of about $1.5 \times 10^7$ vesicles/Kg.

The vesicle compositions are generally administered over a period of time which may vary and depends upon a variety of factors including, for example, the volume of the vesicle composition being administered, the weight of the patient, the particular lipids, polymers, proteins, vesicles, gases or gaseous precursors employed in the composition, the purpose for the administration (for example, diagnostic or therapeutic), the region of interest, the mode of administration, the size of the vesicles, and the like. An exemplary administration time for the vesicle compositions is about 5 seconds. Dividing the vesicle dose by this time period provides an administration rate which may be expressed as vesicles/Kg-sec. Thus, the vesicle dose ($1.5 \times 10^7$ vesicles/Kg) and administration time (5 sec) described above provides a vesicle administration rate of about $3 \times 10^6$ vesicles/Kg-sec. The preferred mode of administration is by infusion.

It is to be understood that the foregoing specific vesicle concentrations, composition doses, administration times and administration rates are for purposes of illustration only, and not for purposes of limitation.

For imaging uses of the present invention, a separately added diagnostic bioactive agent need not necessarily be employed with the gaseous precursor and/or stabilizing material. Indeed, in many applications (e.g., ultrasound), the conversion of the gaseous precursor into a gas at the region of elevated temperature will in itself allow and/or facilitate visualization of the region, resulting in a visible and/or enhanced visible image of the region or any diseased tissue in the region, or other useful data readout or image. Of course, if desired, an additional diagnostic bioactive agent may be employed. Suitable contrast agents useful as additional diagnostic agents will be readily apparent to one skilled in the art.

The following examples are illustrative of the present invention and should not be considered limiting the scope of the invention in any way. Examples 1, 3–5, 9, 11, 12 and 17 are actual examples, while Examples 2, 6–8, 10, 13–16, 18 and 19 are prophetic. All lipids used in the examples were obtained from Avanti Polar Lipids, Alabaster, Ala.

EXAMPLES

Example 1

Two milliliters (ml) of perfluorohexane (PCR, Inc., Gainesville, Fla.) was mixed with 1 milligram (mg) dexamethasone-21 acetate (Sigman Chemical Co., St. Louis, Mo.). The mixture was sonicated using a Heat Systems (Farmingdale, N.Y.) Probe Sonicator at a power level setting of 5. The dexamethasone was noted to precipitate out within the perfluorohexane to form small microcrystals. The mixture was placed within a 37° C. water bath. The perfluorohexane did not vaporize, and no acoustic change was observed on ultrasound.

Example 2

A lipid blend consisting of 82 mole percent dipalmitoylphosphatidylcholine, 8 mole percent dipalmitoylphosphatidic acid, and 10 mole percent dipalmitoylphosphatidylethanolamine-PEG 5000 is combined with dexamethasone-21 acetate in methanol, to yield a concentration of 10 mg of lipid per mL and 10 mg of dexamethasone per mL in methanol. The materials are mixed thoroughly and then evaporated to dryness and lyophilized. The lipid blend with dexamethasone is resuspended in sterile, filtered, deionized water and then, after thorough mixing, is again lyophilized. The resulting lipid blend is then suspended in normal saline at a concentration of 10 mg/mL. To eliminate larger vesicles the material is then put through an extruder (Lipex Biomembranes, Vancouver, B.C. Canada), under 1000 psi nitrogen. The material is passed through a 2 micrometer ($\mu$m) filter then five times through a 0.4 $\mu$m filter. The filtered material is then sized by a quasi-elastic light scattering device (Particle Sizing Systems, Santa Barbara, Calif.). The mean diameter of the particles is about 200–500 nanometers.

Example 3

Dipalmitoyl ethyl phosphocholine (DPEPC) was mixed with dioleoylphosphatidylethanolamine (DOPE) at a 1:1 mole ratio. The lipids were mixed in sterile, deionized water and the mixture was then lyophilized. The lipids were resuspended at a concentration of 1.0 mg/mL again in sterile deionized water, and then mixed with perfluorohexane at a concentration of 10 $\mu$l/mL. The material was then extruded as described in Example 2. To achieve transfection, DNA (chloramphenical transacetylase gene (CAT), Promega, Madison, Wis.) with cauliflower mosaic virus promoter (CMV) (Life Technologies, Gaithersburg, Md.) was mixed with the lipid particles at a concentration of 1.0 mg/mL and applied to the HeLa cells. The concentration of CMV was determined by protein assay of expressed chloramphenicol transacetylase. The results are summarized below. Concentration is expressed in nanograms per mL.

| Sample | CMV concentration (std. deviation) |
| --- | --- |
| HeLa cells (control) | −38.147 (7.78) |
| DPEPC/DOPE | 665.86 (97.12) |
| DPEPC/DOPE/perfluorohexane | 1424.043 (56.47) |

As indicated, DPEPC/DOPE/perfluorohexane more than doubled the rate of efficiency as compared with lipids without perfluorohexane.

Example 4

The procedure of Example 1 was repeated, except that of 1-bromoperfluorobutane was substituted for perfluorohexane The mixture was sonicated to form small particles. Under light microscopic observation (500× magnification), crystal aggregates of dexamethasone-21 were observed.

Example 5

Figure 3:
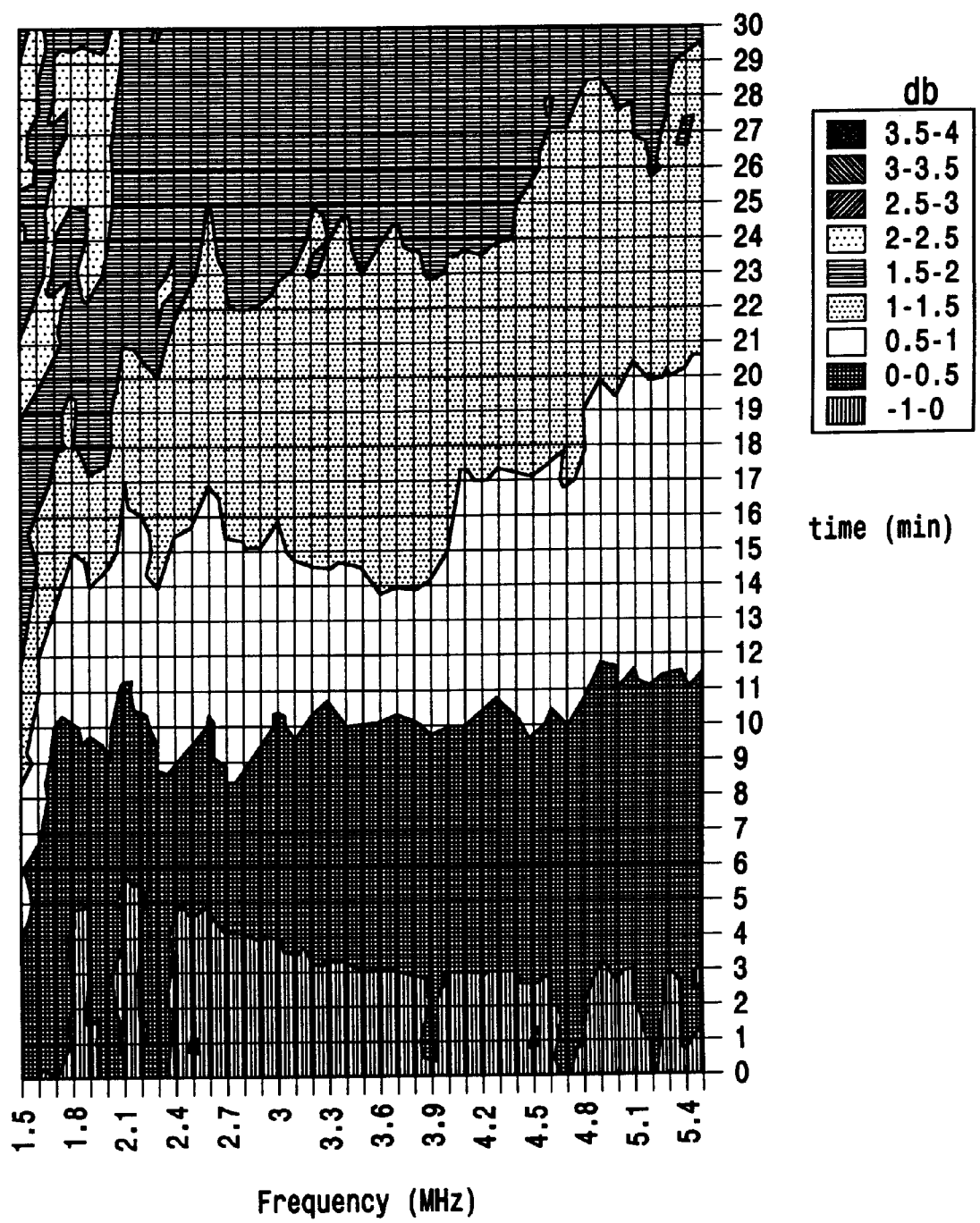
FIG. 3 is a representation of the acoustic activity of a dispersion of 1-bromoperfluorobutane in water plotted against time. The traces show increasing dB reflectivity as a response to scanning with ultrasound energy.

50 microliters ($\mu$l) of 1-bromoperfluorobutane was mixed with 5 mL of the lipid blend described in Example 2, to yield a concentration of 1.0% (V/V) suspension of 1-bromoperfluorobutane in ethanol. The mixture was shaken on a Wig-L-Bug (Crescent Dental, Lyons, Ill.), then extruded through an extruder device (Lipex Biomembranes, Vancouver, B.C., Canada). During shaking and extrusion the mixture was maintained at a temperature of about 0–5° C. by immersion in an ice water bath. A dispersion was formed, of particles having a bimodal size distribution with maxima at 99.5 nm and 906.4 nm. Under sustained ultrasonic scanning, a power level of about 10 percent of the power used in conventional diagnostic ultrasound produced a 1.0 db acoustic scattering response. FIG. 3 shows the acoustic activity of 1-bromononafluorobutane.

Example 6

A copolymer of poly-d-L-lactide (prepared from the monomeric units of d-lactide and L-lactide) is dissolved in diethyl ether at a polymer concentration of 10 mg/mL. To the copolymer diethylether mixture is added perfluorohexane to yield a perfluorohexane concentration of 2 mg/mL. The mixture is maintained in an ice water bath and agitated vigorously by sonication for about 5 minutes. Water is then added to yield approximately 10 parts water for every one part ether. The mixture is then shaken in a Wig-L-Bug, producing a perfluorohexane-in-ether-in-water emulsion, equivalent to an oil-in-oil-in-water emulsion. The temperature is gradually increased from 25° C. to 30° C. resulting in evaporation of the ether phase. The poly-d-L-lactide copolymer precipitates out on the surface of the perfluorohexane, resulting in a suspension of perfluorohexane microspheres coated by a polymeric shell of poly-d-L-lactide.

Example 7

Dexamethasone is crystallized in perfluorohexane, and poly-d-L-lactide copolymer is dissolved in diethyl ether as in Example 6. To the copolymer diethyl ether mixture is then added the desamethasone perfluorohexane mixture to yield a perfluorohexane concentration of 1.0 mg/mL. Evaporation of the ether phase results in precipitation of poly-d-L-lactide copolymer on the surface of perfluorohexane, and dexamethasone crystals in the nanometer diameter range (nanocrystals) contained within the perfluorohexane.

Example 8

A copolymer of poly-d-L-lactide is dissolved in methylethyl ether (b.p. 10.8° C.) at a polymer concentration of 10 mg/mL. To the mixture is added 1-bromoperfluorobutane to yield a perfluorohexane concentration of 2 mg/mL. The mixture is maintained in an ice water bath and agitated vigorously by sonication, as in Example 6. Water is then added to yield approximately 10 parts water for every one part ether. The mixture is then shaken in a Wig-L-Bug, producing a 1-bromoperfluorobutane-in-ether-in-water emulsion, equivalent to an oil-in-oil-in-water emulsion. The temperature is gradually increased and the pressure reduced resulting in evaporation of the ether phase. The poly-d-L-lactide copolymer precipitate out on the surface of the 1-bromoperfluorobutane, resulting in a suspension of 1-bromoperfluorobutane microspheres coated by a polymeric shell of poly-d-L-lactide.

Example 9

Lipid aggregates were formed by the following procedure: Dry (lyophilized) lipids were hydrated in deionized water by heating and stirring, in the following mole percentage ratio: 70 mole percent dimyristoylphosphatidylcholine (DMPC)/20 mole percent dimyristoylphosphatidic acid (DMPA)/10 mole percent dimyristoylphosphatidylethanolamine (DMPE) with a polyethylene group of 5000 molecular weight (5000 dalton unit) attached thereto (DMPE-PEG5000). Approximately 5 milligrams of the lyophilized lipid blend was heated to about 45–50° C. for 1 hour and sonicated in an Aquasonic cleaner Model 75 HT (VWR Scientific Co., Cerritos, Calif.) at room temperature for 30 minutes. Sonication was then resumed for another 30 minutes. Perfluorohexane (10 mg/mL) was added to the mixture, and the mixture then agitated in a Wig-L-Bug. As a result of the sonication and agitation the size of the lipid particles was reduced from a range of about 0.5 to about 10 microns to an entire population of particles under 2 microns. Half of the solution was then combined with an equal volume of 20 millimolar $CaCl_2$ which had been triply filtered through a 2.2 micrometer filter, to yield a final concentration of 0.5 mg/mL lipid and 10 mL $CaCl_2$. The particle size was determined using a NICOMP C370 (Particle Sizing Systems, Santa Barbara Calif.), using a standard modified NNLS/CONTIN algorithm.

Example 10

Lipid aggregates of the nanometer size (nanoaggregates) are formed according to the procedure of Example 9, with the exception that 1-bromoperfluorobutane is added to the lipid mixture before the heating and sonication step. The aggregates are lyophilized, which results in porous, solid structures. The structures may be stored under a head space of air or insoluble gas, such as perfluoropropane or sulfur hexafluoride, to produce porous gas-filled particles. Bioactive agents may be incorporated into the particles by adding the desired amount of bioactive agent either before or during or after reconstitution (rehydration).

Example 11

Figure 4:
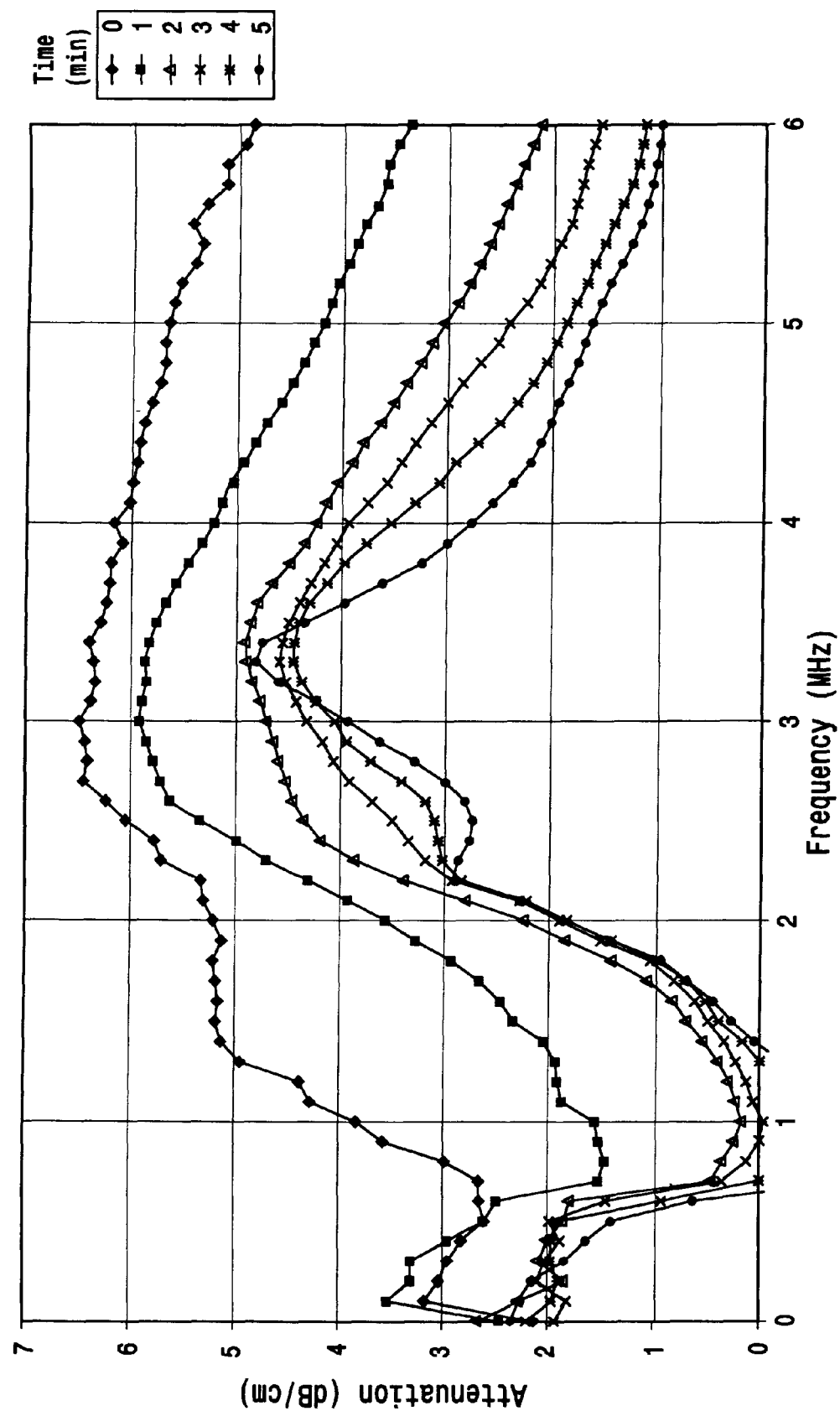
FIG. 4 is a representation of the acoustic scattering of a dispersion of 15% dexamethasone prodrug in 69.7% DPPC, 6.8% DPPA, 8.5% DPPE-PEG-5000 with a head space containing gaseous perfluoropropane. Data was collected at one minute intervals from 0–5 minutes.

Lipids in dry powder form were combined in the following mole percentage ratio: 67.8% DPPC/6.8% DPPA/8.5% DPPE-PEG-5000/15% dexamethasone prodrug in a stoppered glass vial. The lipids were mixed thoroughly then evaporated to dryness, lyophilized, then resuspended in sterile, filtered deionized water. After thorough mixing, the mixture was again lyophilized. The lipid blend was then suspended in a normal saline/propylene glycol/glycerol solution (8:1:1) at a lipid concentration of 10 mg/mL. Perfluorobutane was added to fill the head space above the mixture. The solution was then shaken in a Wig-L-Bug and extruded (Lipex Biomembranes, Vancouver, B.C., Canada) under 1000 psi nitrogen. The extruded material was passed through a 2 micrometer filter, then through a 1 micrometer filter, then through a 0.4 micrometer filter five times. The size of the lipid particles was determined by quasi-elastic light scattering (Particle Sizing Systems, Santa Barbara, Calif.). The mean diameter was about 3440 nm, with a standard deviation of 680 nanometers. The acoustic scattering was plotted (FIG. 4) and showed a peak attenuation of 6.5 db at 3 MHz.

Example 12

Lipids in dry powder form were combined in the following mole percentages in a stoppered glass vial: 67.8% DPPC, 6.8% DPPA, 8.5% DPPE-PEG-5000, and 15% dexamethasone. The blend was mixed thoroughly then evaporated to dryness, lyophilized, and resuspended in sterile, filtered, deionized water. After thorough mixing, the mixture was again lyophilized, then resuspended in an 8:1:1: normal saline/propylene glycol/glycerol solution, to yield a lipid concentration of 10 mg/mL. Perfluorobutane was added to fill the head space above the mixture. The mixture was then shaken in a Wig-L-Bug and extruded and filtered according to the procedure in Example 11, yielding a light frothy upper bubble phase substantially separate from a denser homogeneous liquid phase. Assay by ultraviolet spectrophotometry showed that the amount of dexamethasone associated with the upper bubble phase is 2.72 times that associated with the lower liquid phase, confirming that the dexamethasone is effectively trapped within the lipid coated perfluorobutane bubbles.

Example 13

Lipids are combined in the following mole percentage ratio: 67.8% DPPC/6.8% DPPA/8.5% DPPE-PEG-5000/15% dexamethasone prodrug in a stoppered glass vial. The lipids are mixed thoroughly then evaporated to dryness, lyophilized, then resuspended in sterile, filtered deionized water. After thorough mixing, the mixture is again lyophilized. The lipid blend is then suspended in a normal saline/propylene glycol/glycerol solution (8:1:1) at a lipid concentration of 10 mg/mL. 1-bromoperfluorobutane was added to fill the head space above the mixture. The solution is then shaken in a Wig-L-Bug and extruded (Lipex Biomembranes, Vancouver, B.C., Canada) under 1000 psi nitrogen. The extruded material is passed through a 2 micrometer filter, then through a 1 micrometer filter, then through a o.4 micrometer filter five times. The size of the lipid particles is determined by quasi-elastic light scattering (Particle Sizing Systems, Santa Barbara, Calif.).

Example 14

A mixture of lipids and 1-bromoperfluorobutane is formed as in Example 13, to yield a lipid concentration of 10 mg/mL and a 1-bromoperfluorobutane concentration of 2.5 mg/mL. The mixture is microemulsified using a microfluidizer device (Microfluidics, Newton, Mass.) at a pressure of 8000 psi for twenty passes. During microfluidization the mixing chamber is immersed in an ice water bath to maintain a temperature of about 0–5° C.

Example 15

Dexamethasone prodrug is suspended in perfluorohexane to yield a perfluorohexane concentration of 1.0 mg/mL, with about 10 weight percent pluronic F50 (Spectrum Chemical, Gardena, Calif.) (a copolymer of hydroxypoly(oxyethylene) polyoxypropylene) added to stabilized the dexamethasone prodrug. A copolymer of poly-d-L-lactide is dissolved in diethyl ether at a polymer concentration of 10 mg/mL. To the mixture is added the perfluorohexane suspension of dexamethasone prodrug to yield a polymer concentration of 2 mg/mL. The mixture is maintained in an ice water bath and agitated vigorously by sonication. Water is then added to yield approximately 10 parts water for every one part ether. The mixture is then shaken in a Wig-L-Bug as in Example 6. The temperature is gradually increased and the pressure reduced resulting in evaporation of the ether phase. The poly-d-L-lactide copolymer precipitates out on the surface of the perfluorohexane, resulting in a suspension of dexamethasone prodrug within perfluorohexane microspheres, coated by a polymeric shell of poly-d-L-lactide.

Example 16

In a 4° C. cold room, under a nitrogen hood, dexamethasone prodrug is suspended in 1-bromoperfluorobutane to yield a l-bromoperfluorbutane concentration of 1.0 mg/mL, with about 10 weight percent pluronic F50 (Spectrum Chemical, Gardena, Calif.) added to stabilized the dexamethasone prodrug. A copolymer of poly-d-L-lactide is dissolved in methylethyl ether (b.p. 10.8° C.) at a polymer concentration of 10 mg/mL. To the mixture is added the perfluorohexane suspension of dexamethasone prodrug to yield a polymer concentration of 2 mg/mL. The mixture is maintained in an ice water bath and agitated vigorously by sonication. Water is then added to yield approximately 10 parts water for every one part ether. The mixture is then shaken in a Wig-L-Bug as in Example 6. The temperature is gradually increased and the pressure reduced resulting in evaporation of the ether phase. The poly-d-L-lactide copolymer precipitates out on the surface of the 1-bromoperfluorubutane, resulting in a suspension of dexamethasone prodrug within 1-bromoperfluorubutane microspheres, coated by a polymeric shell of poly-d-L-lactide. The use of the lower-boiling methylethyl ether rather than ethyl ether allows for increased retention of the perfluorocarbon within the poly-d-L-lactide shell during evaporation of the ether.

Example 17

Amphotericin B (Bristol-Myers Squibb, Princeton, N.J.) was dissolved in soybean oil at 2 mg/ml. 1.5 mls of the lipid mixture from Example 13 was mixed with 80 μl of Amphotericin-B solution and 7.5 μl of Pluronic F-68 (Spectrum Chem., Gardena, Calif.) was added. The headspacee of the vial was evacuated by vacuum and replaced with perfluorobutane. The mixture was shaken for one minute on an ESPE-Capmix. The bubbles visible incorporated Amphotericin as demonstrated by their yellow color. They were acoustically active and had a weighted mean size of 1.5 μm.

Example 18

Example 17 is repeated using 1-bromononafluorobutane in place of perfluorobutane.

Example 19

Example 18 is repeated substituting indomethacin (Merck, Inc., Rahway, N.J.) for amphotericin-B with the shaking performed at 50° C. to gas-instill the micro spheres.

The disclosures of each patent, patent application and publication cited or described herein are hereby incorporated by reference herein, in their entirety.

Various modifications, in addition to those described herein, will be apparent to those skilled in the art from the foregoing description. Such modifications are also intended to fall within the scope of the appended claims.

What is claimed is:

1. A method for delivering a bioactive agent to a region of elevated temperature in a patient comprising administering to the patient a composition comprising a bioactive agent and a gaseous precursor which undergoes a phase transition to a gas at said region of elevated temperature in the absence of an application of external heat.

2. A method according to claim 1 wherein said gaseous precursor is an organic halide.

3. A method according to claim 2 wherein said halide in said gaseous precursor is selected from the group consisting of fluorine, chlorine and bromine.

4. A method according to claim 3 wherein said halide in said gaseous precursor is fluorine.

5. A method according to claim 4 wherein said gaseous precursor is selected from the group consisting of 3-fluorobenzaldehyde, 2-fluoro-5-nitrotoluene, 3-fluorostyrene, perfluoro-2-methyl-2-pentene, 3,5-difluoroaniline, 2,2,2-trifluoroethylacrylate, 3-(trifluoromethoxy)-acetophenone, 1,1,2,2,3,3,4,4-octafluorobutane, 1,1,1,3,3-pentafluorobutane, perfluorocyclohexane, perfluoromethyl-n-butyl ether, perfluoromethylisopropyl ether, perfluoromethyl-t-butyl ether, 1-fluorobutane, 1-bromononafluorobutane, 4-trifluoromethyl perfluorotetrahydrofuran, perfluorotetrahydropyran, and perfluoropentane.

6. A method according to claim 3 wherein said halide in said gaseous precursor is bromine.

7. A method according to claim 6 wherein said gaseous precursor is selected from the group consisting of: 1-bromoethane, 6-bromo-1-hexene, 2-bromo-2-nitropropane, 2-bromo-5-nitrothiophene, and 2-bromopropene.

8. A method according to claim 3 wherein said halide in said gaseous precursor is chlorine.

9. A method according to claim 8 wherein said gaseous precursor is selected from the group consisting of 3-chloro-5,5-dimethyl-2-cyclohexene and 2-chloro-2-methylpropane.

10. A method according to claim 2 wherein said gaseous precursor is selected from the group consisting of 1-chloro-1-fluoro-1-bromomethane, 1,1,1-trichloro-2,2,2-trifluoroethane, 1,2-dichloro-2,2-difluoroethane, 1,1-dichloro-1,2-difluoroethane, 1,2-dichloro-1,1,3-trifluoropropane, 1,1,2,2,3,3,4,4-octafluorobutane, 1,1,1,3,3-pentafluorobutane, 1-bromoperfluorobutane, 1-bromo-2,4-difluorobenzene, 2-iodo-1,1,1-trifluoroethane, 5-bromovaleryl chloride, 1,3-dichlorotetrafluoroacetone, bromine pentafluoride, 1-bromo-1,1,2,3,3,3-hexafluoropropane, 2-chloro-1,1,1,4,4,4-hexafluoro-2-butene, 2-chloropentafluoro-1,3-butadiene, iodotrifluoroethylene, 1,1,2-trifluoro-2-chloroethane, 1,2-difluorochloroethane, 1,1-difluoro-2-chloroethane, 1,1-dichlorofluoroethane, and heptafluoro-2-iodopropane.

11. A method according to claim 1 wherein the phase transition temperature of said gaseous precursor is from about 28.5° C. to about 56° C.

12. A method according to claim 11 wherein the phase transition temperature of said gaseous precursor is from about 35° C. to about 52° C.

13. A method according to claim 12 wherein the phase transition temperature of said gaseous precursor is from about 37° C. to about 48° C.

14. A method according to claim 13 wherein the phase transition temperature of said gaseous precursor is from about 38° C. to about 42° C.

15. A method according to claim 1 further comprising a stabilizing material and wherein said stabilizing material is selected from the group consisting of lipids, polymers, proteins, and surfactants.

16. A method according to claim 15 wherein said stabilizing material comprises lipids.

17. A method according to claim 16 wherein said lipids comprise phospholipids.

18. A method according to claim 17 wherein said phospholipids are selected from the group consisting of phosphatidylcholine, phosphatidylethanolamine and phosphatidic acid.

19. A method according to claim 18 wherein said phosphatidylcholine is selected from the group consisting of dioleoylphosphatidylcholine, dimyristoylphosphatidylcholine, dipalmitoylphosphatidylcholine and distearoylphosphatidylcholine.

20. A method according to claim 19 wherein said phosphatidylcholine comprises dipalmitoylphosphatidylcholine.

21. A method according to claim 18 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

22. A method according to claim 18 wherein said phosphatidylethanolamine comprises dipalmitoylphosphatidylethanolamine.

23. A method according to claim 18 wherein said phosphatidic acid comprises dipalmitolylphosphatidic acid.

24. A method according to claim 15 wherein said stabilizing material comprises proteins.

25. A method according to claim 24 wherein said proteins comprise albumin.

26. A method according to claim 15 wherein said stabilizing material comprises polymers.

27. A method according to claim 26 wherein said polymers comprise a hydrophilic polymer.

28. A method according to claim 27 wherein said hydrophilic polymer comprises polyethylene glycol.

29. A method according to claim 26 wherein said polymers comprise synthetic polymers or copolymers which are prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, E-caprolactone, acrolein, cyanoacrylate, cyanomethacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethyl-methacrylate, vinyl pyridine, aminoethyl methacrylates, lactides, and 2-methacryloyloxytrimethyl-ammonium chloride.

30. A method according to claim 29 wherein said polymers comprise synthetic polymers or copolymers selected from the group consisting of polyacrylic acid, polyethyleneimine, polymethacrylic acid, polymethylmethacrylate, polycyanomethacrylate, polysiloxane, polydimethylsiloxane, polylactic acid, poly($\epsilon$-caprolactone), epoxy resin, poly(ethylene oxide), poly(ethylene glycol), polyamide, polyvinylidene-polyacrylonitrile, polyvinylidene-polyacrylonitrile-polymethylmethacrylate, polylactide coglycolide, nylon and polystyrene-polyacrylonitrile.

31. A method according to claim 30 wherein said polymers comprise polycyanomethacrylate.

32. A method according to claim 15 wherein said stabilizing material comprises a surfactant.

33. A method according to claim 32 wherein the surfactant is selected from the group consisting of perfluorinated alkylated surfactants and fluorine-containing carbohydrates.

34. A method according to claim 15 wherein said stabilizing material is in the form of a vesicle.

35. A method according to claim 34 wherein said vesicles are selected from the group consisting of micelles and liposomes.

36. A method according to claim 34 wherein said vesicles are formulated from lipids.

37. A method according to claim 36 wherein said lipids comprise phospholipids.

38. A method according to claim 37 wherein said phospholipids are selected from the group consisting of phosphatidylcholine, phosphatidylethanolamine and phosphatidic acid.

39. A method according to claim 38 wherein said phosphatidylcholine is selected from the group consisting of dioleoylphosphatidylcholine, dimyristoylphosphatidylcholine, dipalmitoylphosphatidylcholine and distearoylphosphatidylcholine.

40. A method according to claim 39 wherein said phosphatidylcholine comprises dipalmitoylphosphatidylcholine.

41. A method according to claim 38 wherein said phosphatidylethanolamine is selected from the group consisting of dipalmitoylphosphatidylethanolamine, dioleoylphosphatidylethanolamine, N-succinyldioleoylphosphatidylethanolamine and 1-hexadecyl-2-palmitoylglycerophosphoethanolamine.

42. A method according to claim 41 wherein said phosphatidylethanolamine comprises dipalmitoylphosphatidylethanolamine.

43. A method according to claim 38 wherein said phosphatidic acid comprises dipalmitolylphosphatidic acid.

44. A method according to claim 38 wherein said lipid further comprises a polymer.

45. A method according to claim 44 wherein said polymer comprises a hydrophilic polymer.

46. A method according to claim 45 wherein said hydrophilic polymer comprises polyethylene glycol.

47. A method according to claim 34 wherein said vesicles comprise proteins.

48. A method according to claim 47 wherein said proteins comprise albumin.

49. A method according to claim 34 wherein said vesicles comprise polymers.

50. A method according to claim 49 wherein said polymers comprise synthetic polymers or copolymers which are prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, E-caprolactone, acrolein, cyanoacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4- pentadiene-1-ol, vinyl acetate, acrylonitrile, styrene, p-aminostyrene, p-aminobenzylstyrene, sodium styrene sulfonate, sodium 2-sulfoxyethylmethacrylate, vinyl pyridine, aminoethyl methacrylates, lactides and 2-methacryloyloxytrimethyl-ammonium chloride.

51. A method according to claim 50 wherein said polymers comprise synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), polyamide, polyvinylidene-polyacrylonitrile, polyvinylidene-polyacrylonitrile-polymethylmethacrylate, polylactide coglycolide, nylon and polystyrene-polyacrylonitrile.

52. A method according to claim 34 wherein said vesicles comprise unilamellar vesicles.

53. A method according to claim 52 wherein said vesicles comprise one monolayer.

54. A method according to claim 34 wherein said vesicles are selected from the group consisting of oligolamellar and multilamellar vesicles.

55. A method according to claim 1 wherein said bioactive agent is selected from the group consisting of pharmaceutical agents, and diagnostic agents.

56. A method according to claim 55 wherein said bioactive agent is a pharmaceutical.

57. A method according to claim 56 wherein the pharmaceutical is selected from the group consisting of antibiotics, hormones, vasoactive compounds, antithrombotics, chemotherapeutic agents, bioactive peptides, mitotic inhibitors, antihelminthics, antimalarials, antituberculosis agents, immune sera, antitoxins, antivenins, vaccines, vitamins, anti-coagulants, antiinflammatory agents, RNA and DNA.

58. A method according to claim 1, further comprising the application of external heat to the region.

59. The method of claim 1 wherein the region of elevated temperature is associated with a condition selected from the group consisting of disease, infection, inflammation, and injury.

60. A method for treating a region of elevated temperature in a patient comprising administering to the patient a composition comprising a pharmaceutical agent and a gaseous precursor which undergoes a phase transition to a gas at said region of elevated temperature in the absence of an application of external heat.

* * * * *

UNITED STATES PATENT AND TRADEMARK OFFICE
CERTIFICATE OF CORRECTION

PATENT NO. : 6,143,276
DATED : November 7, 2000
INVENTOR(S) : Evan C. Unger

It is certified that error appears in the above-identified patent and that said Letters Patent is hereby corrected as shown below:

Title page,
Item [56], U.S. PATENT DOCUMENTS, please delete "5,885,865" and insert
-- 5,855,865 -- therefor.
FOREIGN PATENT DOCUMENTS, "WO/ 84/02909", please delete "8/1994" and insert -- 8/1984 -- therefor.
OTHER PUBLICATIONS, "Yang et al.," please delete "Facture" and insert
-- Fracture -- therefor.
"Keller et al.," please delete "Microcirulation" and insert -- Microcirculation -- therefor.
"Mayhew et al.," please delete "Biochemica" and insert -- Biochimica -- therefor.
"Cheng et al.," please delete "*Investigation*" and insert -- *Investigative* --therefor.
"Fukuda et al.," please delete "Diotadecyldimethylammonium" and insert
-- Dioctadecyldimethylammonium -- therefor.
"Shiina et al.," please delete "Hyperthermiably" and insert -- Hyperthermia by -- therefor.
"Poznansky et al.," please delete "Biologica" and insert -- Biological -- therefor.
"Ter-Pogossian", please delete "*Tomography*, Kee, et al., n."; and after "*Computed Body*", please insert -- *Tomography*, Lee et al., -- therefor.
"Aronberg", please delete "Kee" and insert -- Lee -- therefor.
"Frézard et al.," please delete "Fluorniated" and insert -- Fluorinated -- therefor.

Column 10,
Line 45, please delete "$CF_3O(CF)_2CF_3$" and insert -- $CF_3O(CF_2)_2CF_3$ -- therefor.
Line 46, please delete "$(CF)_2$" and insert -- $(CF_3)_2$ -- therefor.

Column 14,
Lines 58-66, please delete

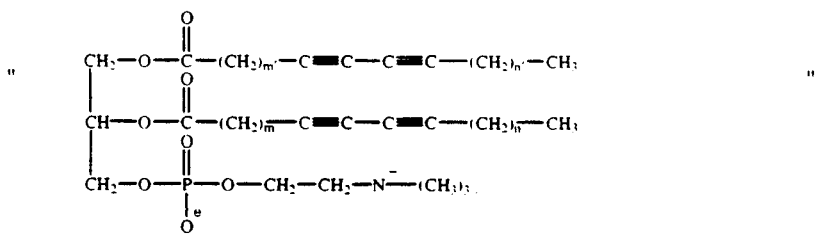

UNITED STATES PATENT AND TRADEMARK OFFICE
CERTIFICATE OF CORRECTION

PATENT NO. : 6,143,276
DATED : November 7, 2000
INVENTOR(S) : Evan C. Unger

It is certified that error appears in the above-identified patent and that said Letters Patent is hereby corrected as shown below:

Column 14, cont'd,
Lines 58-66, please insert

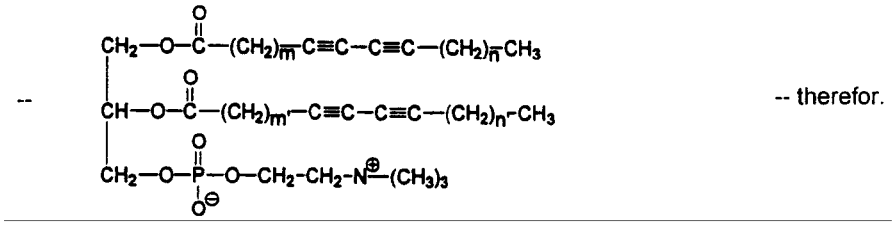

-- therefor.

Column 16,
Line 58, please delete "(pb$^{+2}$" and insert -- (Pb$^{+2}$ -- therefor.

Column 17,
Line 32, please delete "sphinolipids" and insert -- sphingolipids -- therefor.
Line 46, please delete "(dodecyaminocarbonylmethylene)..." and insert
-- (dodecylaminocarbonylmethylene)... -- therefor.

Column 20,
Line 43, please delete "perfluorotripopylamine" and insert
-- perfluorotripropylamine -- therefor.

Column 24,
Line 30, please delete "Microfluidizerm" and insert -- Microfluidizer$^{TM}$ -- therefor.

Column 29,
Line 16, please delete "...[3/4π3/4 · [πr$_{gas}^3$..." and insert -- ...[3/4π[4/3·[πr $_{gas}^3$... -- therefor.

Column 30,
Line 10, please delete "$X_b = \Delta H_{fus}/...$" and insert -- $X^b = \Delta H_{fus}/...$ -- therefor.

Line 11, please delete "At" and insert -- $\Delta T$ -- therefore.

UNITED STATES PATENT AND TRADEMARK OFFICE
CERTIFICATE OF CORRECTION

PATENT NO. : 6,143,276
DATED : November 7, 2000
INVENTOR(S) : Evan C. Unger

It is certified that error appears in the above-identified patent and that said Letters Patent is hereby corrected as shown below:

Column 32,
Line 59, please delete "from 5 about" and insert -- from about -- therefor.

Column 36,
Line 52, please delete "nafcililn" and insert -- nafcillin -- therefor.
Line 58, please delete "difluisal" and insert -- diflunisal -- therefor.

Column 37,
Line 4, please delete "amorbarital" and insert -- amorbarbitol -- therefor.
Line 10, please delete "tulbutal" and insert -- talbutal -- therefor.

Column 41,
Line 58, please delete " $1 \times 10^{-4}$" and insert -- $1 \times 10^{-6}$ -- therefor.

Column 47,
Line 52, please delete "spacee" and insert -- space -- therefor.

Signed and Sealed this

Ninth Day of March, 2004

JON W. DUDAS
*Acting Director of the United States Patent and Trademark Office*